United States Patent [19]
Kerrigan et al.

[11] Patent Number: 6,114,334
[45] Date of Patent: Sep. 5, 2000

[54] PIPERAZINE DERIVATIVES AS THERAPEUTIC AGENTS

[75] Inventors: Frank Kerrigan; Sharon Crawford Cheetham; John Paul Watts, all of Nottingham, United Kingdom

[73] Assignee: Knoll Aktiengesellschaft, Ludwigshafen, Germany

[21] Appl. No.: 08/973,843

[22] PCT Filed: Jul. 2, 1996

[86] PCT No.: PCT/EP96/02889

§ 371 Date: Dec. 17, 1997

§ 102(e) Date: Dec. 17, 1997

[87] PCT Pub. No.: WO97/03067

PCT Pub. Date: Jan. 30, 1997

[30] Foreign Application Priority Data

Jul. 13, 1995 [GB] United Kingdom .................... 9514389
Mar. 29, 1996 [GB] United Kingdom .................... 9606674

[51] Int. Cl.⁷ ........................ A61K 31/496; C07D 403/06
[52] U.S. Cl. ........................ 514/252; 514/254; 544/295; 544/364; 544/371
[58] Field of Search ..................... 544/295, 364, 544/371; 514/252, 254

[56] References Cited

U.S. PATENT DOCUMENTS

| | | | |
|---|---|---|---|
| 3,729,474 | 4/1973 | Mentrup et al. | 260/268 |
| 4,772,604 | 9/1988 | Van Wijngaarden et al. | 544/371 |
| 5,194,437 | 3/1993 | Peglion et al. | 514/254 |
| 5,242,925 | 9/1993 | Boettcher et al. | 514/254 |
| 5,292,739 | 3/1994 | Merce-Vidal et al. | 544/371 |
| 5,418,237 | 5/1995 | Boettcher et al. | 514/253 |
| 5,712,392 | 1/1998 | Thurrauf et al. | 544/364 |
| 5,760,225 | 6/1998 | Yuan | 544/371 |

FOREIGN PATENT DOCUMENTS

| | | |
|---|---|---|
| 395 312 | 10/1990 | European Pat. Off. . |
| 482 696 | 4/1992 | European Pat. Off. . |
| 2289464 | 11/1995 | United Kingdom . |
| 96/02246 | 2/1996 | WIPO . |
| 96/10568 | 4/1996 | WIPO . |

OTHER PUBLICATIONS

Yan Tol et al, *Nature*, vol. 350, p. 610–614 (1991).
Drug Evaluations by AMA, p. 575–579 (1993).
Saxena, *Pharmac. Ther.* 66, p 339–368 (1995).

*Primary Examiner*—Richard L. Raymond
*Attorney, Agent, or Firm*—Keil & Weinkauf

[57] ABSTRACT

Substituted piperazine compounds of formula I

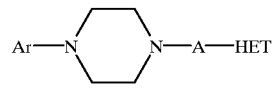

in which HET is a substituted pyrazole, imidazole or 1,2,4-triazole have utility in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity.

8 Claims, No Drawings

PIPERAZINE DERIVATIVES AS THERAPEUTIC AGENTS

This application is a 371 of PCT/EP96/02889, filed Jul. 7, 1996.

The present invention relates to novel substituted piperazine compounds which have affinity for 5-HT$_{1A}$ and/or $\alpha_1$ and/or $\alpha_2$ and/or D$_2$ receptors, to processes for their preparation, to pharmaceutical compositions containing them and to their use in the treatment of central nervous system disorders, for example depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity.

The compound 4-allyl-2-(4-phenylpiperazin-1-ylmethyl)-5-(3-pyridyl)-1,2,4-triazol-3(2H,4H)-thione is commercially available. Certain arylpiperazinylalkylenepyrazole compounds which have limited substitution in the pyrazole ring are disclosed generically in co-pending patent application PCT/EP95/02782 (WO9602246) as having affinity for D$_3$ receptors. Such compounds are not included in the present invention.

The present invention comprises compounds of formula I

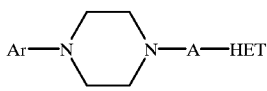

including pharmaceutically acceptable salts thereof, in which

Ar represents phenyl, pyridyl, pyrimidinyl, naphthyl, 1,4-benzodioxin-5-yl, 1,4-benzodioxan-5-yl, benzo[b]furan-7-yl, 2,3-dihydrobenzo[b]furan-7-yl, benzo[b]thiophen-7-yl, 2,3-dihydrobenzo[b]thiophen-7-yl or chroman-8-yl each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms;

A represents an alkylene chain containing 1 to 6 carbon atoms each of which may be optionally substituted by one or two alkyl groups each containing 1 to 3 carbon atoms; and HET represents a group of formula a)–d)

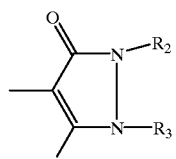

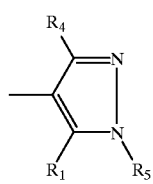

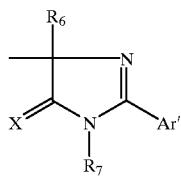

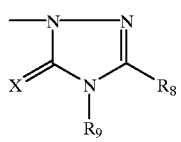

in which R$_1$ represents hydroxy, an alkoxy group containing 1 to 3 carbon atoms, or an amino group optionally substituted by one or two alkyl groups each containing 1 to 3 carbon atoms;

R$_2$ and R$_3$ independently represent an alkyl group containing 1 to 6 carbon atoms optionally substituted by one or more halo, an alkenyl group containing 2 to 6 carbon atoms optionally substituted by one or more halo, a cycloalkyl group containing 3 to 6 carbon atoms, or phenyl, benzyl or a 5 or 6-membered heteroaryl group containing 1 to 3 heteroatoms selected from O,N and S wherein the phenyl, benzyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms;

R$_4$ and R$_5$ independently represent an alkyl group containing 1 to 6 carbon atoms optionally substituted by one or more halo, an alkenyl group containing 2 to 6 carbon atoms optionally substituted by one or more halo, a cycloalkyl group containing 3 to 6 carbon atoms, an amino group optionally substituted by one or two alkyl groups each containing 1 to 3 carbon atoms, or phenyl, benzyl or a 5 or 6-membered heteroaryl group containing 1 to 3 heteroatoms selected from O,N and S wherein the phenyl, benzyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; provided that when either $R_4$ or $R_5$ is alkyl or an amino group optionally substituted by one or two alkyl groups, then the other of $R_4$ or $R_5$ is not alkyl or an amino group optionally substituted by one or two alkyl groups;

$R_6$ represents H or an alkyl group containing 1 to 3 carbon atoms optionally substituted by one or more halo;

$R_7$ represents H, an alkyl group containing 1 to 6 carbon atoms optionally substituted by one or more halo, an alkenyl group containing 2 to 6 carbon atoms optionally substituted by one or more halo, an alkoxyalkyl group containing 2 to 6 carbon atoms optionally substituted by one or more halo, or phenyl, benzyl, a 5 or 6-membered heteroaryl group containing 1 to 3 heteroatoms selected from O, N and S, or phenoxyalkyl wherein the phenyl, benzyl, heteroaryl group or phenoxyalkyl may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms;

$R_8$ and $R_9$ independently represent H, an alkyl group containing 1 to 6 carbon atoms optionally substituted by one or more halo, an alkenyl group containing 2 to 6 carbon atoms optionally substituted by one or more halo, a cycloalkyl group containing 3 to 6 carbon atoms, an alkoxyalkyl group containing 2 to 6 carbon atoms optionally substituted by one or more halo, or phenyl, benzyl or a 5 or 6-membered heteroaryl group containing 1 to 3 heteroatoms selected from O, N and S wherein the phenyl, benzyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms;

with the proviso that when HET is a group of formula d), X is S, Ar is phenyl, A is methylene, and $R_8$ is pyrid-3-yl, then $R_9$ is other than allyl;

Ar' represents phenyl or a 5 or 6-membered heteroaryl group containing 1 to 3 heteroatoms selected from O, N and S wherein the phenyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; and X represents O or S.

In one group of preferred compounds of formula I (group 1), HET represents a group of formula a), b) or c); Ar represents phenyl, pyridyl, pyrimidinyl, naphthyl, 1,4-benzodioxin-5-yl, 1,4-benzodioxan-5-yl, benzo[b]furan-7-yl, 2,3-dihydrobenzo[b]furan-7-yl, benzo[b]thiophen-7-yl, 2,3-dihydrobenzo[b]thiophen-7-yl or chroman-8-yl each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; A represents an alkylene chain containing 1 to 6 carbon atoms each of which may be optionally substituted by one or two alkyl groups each containing 1 to 3 carbon atoms; $R_1$ represents hydroxy, an alkoxy group containing 1 to 3 carbon atoms, or an amino group optionally substituted by one or two alkyl groups each containing 1 to 3 carbon atoms; $R_2$ and $R_3$ independently represent an alkyl group containing 1 to 6 carbon atoms optionally substituted by one or more halo, an alkenyl group containing 2 to 6 carbon atoms optionally substituted by one or more halo, a cycloalkyl group containing 3 to 6 carbon atoms, or phenyl, benzyl or a 5 or 6-membered heteroaryl group containing 1 to 3 heteroatoms selected from O,N and S wherein the phenyl, benzyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally $\underline{N}$-substituted by one or two alkyl groups each containing 1 to 3 carbon atoms, l) a sulphamoyl or sulphamoylmethyl group each optionally $\underline{N}$-substituted by one or two alkyl groups each containing 1 to 3 carbon atoms, or m) an amino group optionally substituted by one or two alkyl groups each containing 1 to 3 carbon atoms; $R_4$ and $R_5$ independently represent an alkyl group containing 1 to 6 carbon atoms optionally substituted by one or more halo, an alkenyl group containing 2 to 6 carbon atoms optionally substituted by one or more halo, a cycloalkyl group containing 3 to 6 carbon atoms, an amino group optionally substituted by one or two alkyl groups each containing 1 to 3 carbon atoms, or phenyl, benzyl or a 5 or 6-membered heteroaryl group containing 1 to 3 heteroatoms selected from O,N and S wherein the phenyl, benzyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally $\underline{N}$-substituted by one or two alkyl groups each containing 1 to 3 carbon atoms, l) a sulphamoyl or sulphamoylmethyl group each optionally $\underline{N}$-substituted by one or two alkyl groups each containing 1 to 3 carbon atoms, or m) an amino group optionally substituted by one or two alkyl groups each containing 1 to 3 carbon atoms; provided that when either $R_4$ or $R_5$ is alkyl or an amino group optionally substituted by one or two alkyl groups, then the other of $R_4$ or $R_5$ is not alkyl or an amino group optionally substituted by one or two alkyl groups; $R_6$ represents H or an alkyl group containing 1 to 3 carbon atoms optionally substituted by one or more halo; $R_7$ represents H, an alkyl group containing 1 to 6 carbon atoms optionally substituted by one or more halo, an alkenyl group containing 2 to 6 carbon atoms optionally substituted by one or more halo, an alkoxyalkyl group containing 2 to 6 carbon atoms optionally substituted by one or more halo, or phenyl, benzyl, a 5 or 6-membered heteroaryl group containing 1 to 3 heteroatoms selected from O, N and S, or phenoxyalkyl wherein the phenyl, benzyl, heteroaryl group or phenoxyalkyl may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally $\underline{N}$-substituted by one or two alkyl groups each containing 1 to 3 carbon atoms, l) a sulphamoyl or sulphamoylmethyl group each optionally $\underline{N}$-substituted by one or two alkyl groups each containing 1 to 3 carbon atoms, or m) an amino group optionally substituted by one or two alkyl groups each containing 1 to 3 carbon atoms; Ar' represents phenyl or a 5 or 6-membered heteroaryl group containing 1 to 3 heteroatoms selected from O, N and S wherein the phenyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally $\underline{N}$-substituted by one or two alkyl groups each containing 1 to 3 carbon atoms, l) a sulphamoyl or sulphamoylmethyl group each optionally $\underline{N}$-substituted by one or two alkyl groups each containing 1 to 3 carbon atoms, or m) an amino group optionally substituted by one or two alkyl groups each containing 1 to 3 carbon atoms; and X represents O or S.

In more preferred compounds (subgroup 1a) of formula I in group 1, HET represents a group of formula a) in which $R_1$ represents hydroxy, an alkoxy group containing 1 to 3 carbon atoms, or an amino group optionally substituted by one or two alkyl groups each containing 1 to 3 carbon atoms; $R_2$ and $R_3$ independently represent an alkyl group containing 1 to 6 carbon atoms optionally substituted by one or more halo, an alkenyl group containing 2 to 6 carbon atoms optionally substituted by one or more halo, a cycloalkyl group containing 3 to 6 carbon atoms, or phenyl, benzyl or a 5 or 6-membered heteroaryl group containing 1 to 3 heteroatoms selected from O,N and S wherein the phenyl, benzyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; and Ar represents phenyl, pyridyl, pyrimidinyl, naphthyl, 1,4-benzodioxin-5-yl, 1,4-benzodioxan-5-yl, benzo[b]furan-7-yl, 2,3-dihydrobenzo[b]furan-7-yl, benzo[b]thiophen-7-yl, 2,3-dihydrobenzo[b]thiophen-7-yl or chroman-8-yl each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; and A represents an alkylene chain containing 1 to 6 carbon atoms each of which may be optionally substituted by one or two alkyl groups each containing 1 to 3 carbon atoms.

In more preferred compounds of formula I in subgroup 1a, HET represents a group of formula a) in which $R_1$ represents hydroxy, an alkoxy group containing 1 to 3 carbon atoms, or an amino group optionally substituted by one or two alkyl groups each containing 1 to 3 carbon atoms; $R_2$ and $R_3$ independently represent an alkyl group containing 1 to 6 carbon atoms optionally substituted by one or more halo, an alkenyl group containing 2 to 6 carbon atoms optionally substituted by one or more halo, a cycloalkyl group containing 3 to 6 carbon atoms, or phenyl wherein the phenyl group may be optionally substituted by one or more substituents selected from a) halo, b) an alkyl group containing 1 to 3 carbon atoms optionally substituted by one or more halo, or c) an alkoxy group containing 1 to 3 carbon atoms optionally substituted by one or more halo; and Ar represents phenyl, naphthyl, 1,4-benzodioxan-5-yl, or benzo[b]furan-7-yl each of which may be optionally substituted by one or more substituents selected from a) halo, b) an alkyl group containing 1 to 3 carbon atoms optionally substituted by one or more halo, or c) an alkoxy group containing 1 to 3 carbon atoms optionally substituted by one or more halo; and A represents methylene.

In especially preferred compounds of formula I in subgroup 1a, HET represents a group of formula a) in which $R_1$ represents an amino group; $R_2$ represents phenyl optionally substituted by a) halo, b) an alkyl group containing 1 to 3 carbon atoms optionally substituted by one or more halo, or c) an alkoxy group containing 1 to 3 carbon atoms optionally substituted by one or more halo; and $R_3$ represents an alkyl group containing 1 to 4 carbon atoms or allyl; and Ar represents naphthyl, 1,4-benzodioxan-5-yl, benzo[b]furan-7-yl, or phenyl optionally substituted, preferably in the 2-position, by an alkyl group containing 1 to 3 carbon atoms or an alkoxy group containing 1 to 3 carbon atoms; and A is methylene. Most preferably, HET is a group of formula a); $R_1$ is amino; $R_2$ is phenyl; $R_3$ is methyl, propyl or allyl; Ar is 2-methoxyphenyl, 2-isopropoxyphenyl, 2-methylphenyl, naphthyl, benzo[b]furan-7-yl, or 1,4-benzodioxan-5-yl; and A is methylene.

In other more preferred compounds (subgroup 1b) of formula I in group 1, HET represents a group of formula b) in which $R_1$ represents hydroxy, an alkoxy group containing 1 to 3 carbon atoms, or an amino group optionally substituted by one or two alkyl groups each containing 1 to 3 carbon atoms; $R_4$ and $R_5$ independently represent an alkyl group containing 1 to 6 carbon atoms optionally substituted by one or more halo, an alkenyl group containing 2 to 6 carbon atoms optionally substituted by one or more halo, a cycloalkyl group containing 3 to 6 carbon atoms, an amino group optionally substituted by one or two alkyl groups each containing 1 to 3 carbon atoms, or phenyl, benzyl or a 5 or 6-membered heteroaryl group containing 1 to 3 heteroatoms selected from O,N and S wherein the phenyl, benzyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; provided that when either $R_4$ or $R_5$ is alkyl or an amino group optionally substituted by one or two alkyl groups, then the other of $R_4$ or $R_5$ is not alkyl or an amino group optionally substituted by one or two alkyl groups; Ar represents phenyl, pyridyl, pyrimidinyl, naphthyl, 1,4-benzodioxin-5-yl, 1,4-benzodioxan-5-yl, benzo[b]furan-7-yl, 2,3-dihydrobenzo[b]furan-7-yl, benzo[b]thiophen-7-yl, 2,3-dihydrobenzo[b]thiophen-7-yl or chroman-8-yl each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; and A represents an alkylene chain containing 1 to 6 carbon atoms each of which may be optionally substituted by one or two alkyl groups each containing 1 to 3 carbon atoms.

In more preferred compounds of formula I in subgroup 1b, HET represents a group of formula b) in which $R_1$ represents hydroxy, an alkoxy group containing 1 to 3 carbon atoms, or an amino group optionally substituted by one or two alkyl groups each containing 1 to 3 carbon atoms; $R_4$ and $R_5$ independently represent an alkyl group containing 1 to 6 carbon atoms optionally substituted by one or more halo, an alkenyl group containing 2 to 6 carbon atoms optionally substituted by one or more halo, a cycloalkyl group containing 3 to 6 carbon atoms, an amino group optionally substituted by one or two alkyl groups each containing 1 to 3 carbon atoms, or phenyl, benzyl or a 6-membered heteroaryl group containing 1 to 3 N atoms wherein the phenyl, benzyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, or d) cyano; Ar represents phenyl, naphthyl, 1,4-benzodioxan-5-yl, or benzo[b]furan-7-yl, each of which may be optionally substituted by one or more substituents selected from a) halo, b) an alkyl group containing 1 to 3 carbon atoms optionally substituted by one or more halo, or c) an alkoxy group containing 1 to 3 carbon atoms optionally substituted by one or more halo; and A represents methylene.

In especially preferred compounds of formula I in subgroup 1b, HET represents a group of formula b) in which $R_1$ represents an amino group; $R_4$ represents an alkyl group containing 1 to 4 carbon atoms, a cycloalkyl group containing 3 to 5 carbon atoms, an amino group, or phenyl optionally substituted by halo, an alkyl group containing 1 to 3 carbon atoms optionally substituted by one or more halo, or an alkoxy group containing 1 to 3 carbon atoms; $R_5$ represents an alkyl group containing 1 to 4 carbon atoms, or pyridyl, pyrimidinyl, benzyl or phenyl wherein the phenyl is optionally substituted by halo, an alkyl group containing 1 to 3 carbon atoms optionally substituted by one or more halo, or an alkoxy group containing 1 to 3 carbon atoms or cyano; Ar represents benzo[b]furan-7-yl, 1,4-benzodioxan-5-yl or phenyl optionally substituted, preferably in the 2- or 3-position, by halo, an alkyl group containing 1 to 3 carbon atoms optionally substituted by one or more halo, or an alkoxy group containing 1 to 3 carbon atoms; and A is methylene. Most preferably, HET is a group of formula b); $R_1$ is an amino group; $R_4$ is cyclopropyl, cyclobutyl, cyclopentyl, tert-butyl, phenyl or an amino group; $R_5$ is phenyl, 2-chlorophenyl, 4-chlorophenyl, 4-methoxyphenyl, 4-cyanophenyl, benzyl, pyrid-2-yl, pyrid-4-yl, pyrimidin-2-yl, methyl, or tert-butyl; Ar is benzo[b]furan-7-yl, 1,4-benzodioxan-5-yl, 2-methoxyphenyl, 2-isopropoxyphenyl, 3-chlorophenyl, 3-trifluoromethylphenyl or 2-methylphenyl; and A is methylene.

In other more preferred compounds (subgroup 1c) of formula I in group 1, HET represents a group of formula c) in which $R_6$ represents H or an alkyl group containing 1 to 3 carbon atoms optionally substituted by one or more halo; $R_7$ represents H, an alkyl group containing 1 to 6 carbon atoms optionally substituted by one or more halo, an alkenyl group containing 2 to 6 carbon atoms optionally substituted by one or more halo, an alkoxyalkyl group containing 2 to 6 carbon atoms optionally substituted by one or more halo, or phenyl, benzyl, a 5 or 6-membered heteroaryl group containing 1 to 3 heteroatoms selected from O, N and S, or phenoxyalkyl wherein the phenyl, benzyl, heteroaryl group or phenoxyalkyl may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; Ar' represents phenyl or a 5 or 6-membered heteroaryl group containing 1 to 3 heteroatoms selected from O, N and S wherein the phenyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; X represents O or S; and Ar represents phenyl, pyridyl, pyrimidinyl, naphthyl, 1,4-benzodioxin-5-yl, 1,4-benzodioxan-5-yl, benzo[b]furan-7-yl, 2,3-dihydrobenzo[b]furan-7-yl, benzo-[b]thiophen-7-yl, 2,3-dihydrobenzo[b]thiophen-7-yl or chroman-8-yl each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; and A represents an alkylene chain containing 1 to 6 carbon atoms each of which may be optionally substituted by one or two alkyl groups each containing 1 to 3 carbon atoms.

In more preferred compounds of formula I in subgroup 1c, HET represents a group of formula c) in which $R_6$ represents H or an alkyl group containing 1 to 3 carbon atoms optionally substituted by one or more halo; $R_7$ represents H, an alkyl group containing 1 to 6 carbon atoms optionally substituted by one or more halo, an alkenyl group containing 2 to 6 carbon atoms optionally substituted by one or more halo, an alkoxyalkyl group containing 2 to 6 carbon atoms optionally substituted by one or more halo, or phenyl, wherein the phenyl may be optionally substituted by one or more substituents selected from a) halo, b) an alkyl group containing 1 to 3 carbon atoms optionally substituted by one or more halo, or c) an alkoxy group containing 1 to 3 carbon atoms optionally substituted by one or more halo; Ar' represents phenyl or a 5 or 6-membered heteroaryl group containing 1 to 3 N atoms wherein the phenyl or heteroaryl group may be optionally substituted by one or more substituents selected from a) halo, b) an alkyl group containing 1 to 3 carbon atoms optionally substituted by one or more halo, or c) an alkoxy group containing 1 to 3 carbon atoms optionally substituted by one or more halo; X represents O or S; Ar represents phenyl, pyridyl, pyrimidinyl, naphthyl, 1,4-benzodioxan-5-yl, or benzo[b]furan-7-yl, each of which may be optionally substituted by one or more substituents selected from a) halo, b) an alkyl group containing 1 to 3 carbon atoms optionally substituted by one or more halo, or c) an alkoxy group containing 1 to 3 carbon atoms optionally substituted by one or more halo; and A is methylene.

In especially preferred compounds of formula I in subgroup 1c, HET represents a group of formula c) in which $R_6$ represents an alkyl group containing 1 to 3 carbon atoms; $R_7$ represents H, an alkyl group containing 1 to 3 carbon atoms, or an alkenyl group containing 2 to 4 carbon atoms; Ar' represents phenyl or pyridyl which may be optionally substituted by one or more substituents selected from a) halo, b) an alkyl group containing 1 to 3 carbon atoms, or c) an alkoxy group containing 1 to 3 carbon atoms; X represents O; and Ar represents phenyl or 1,4benzodioxan-5-yl each of which may be optionally substituted by one or more substituents selected from a) halo, b) an alkyl group containing 1 to 3 carbon atoms, or c) an alkoxy group containing 1 to 3 carbon atoms; and A is methylene. Most preferably, HET is a group of formula c); $R_6$ is methyl; $R_7$ is H or allyl; Ar' is phenyl or 3-pyridyl; X is O; Ar is 3-chlorophenyl, 3-trifluoromethylphenyl, 2-methylphenyl, 2-methoxyphenyl or 1,4-benzodioxan-5-yl; and A is methylene.

In a second group of preferred compounds of formula I (group 2), HET represents a group of formula d); $R_8$ and $R_9$ independently represent H, an alkyl group containing 1 to 6 carbon atoms optionally substituted by one or more halo, an alkenyl group containing 2 to 6 carbon atoms optionally substituted by one or more halo, a cycloalkyl group containing 3 to 6 carbon atoms, an alkoxyalkyl group containing 1 to 6 carbon atoms optionally substituted by one or more halo, or phenyl, benzyl or a 5 or 6-membered heteroaryl group containing 1 to 3 heteroatoms selected from O, N and S wherein the phenyl, benzyl or heteroaryl group may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; X represents O or S; Ar represents phenyl, pyridyl, pyrimidinyl, naphthyl, 1,4-benzodioxin-5-yl, 1,4-benzodioxan-5-yl, benzo[b]furan-7-yl, 2,3-dihydrobenzo-[b]furan-7-yl, benzo[b]thiophen-7-yl, 2,3-dihydrobenzo-[b]thiophen-7-yl or chroman-8-yl each of which may be optionally substituted by one or more substituents selected from a) halo, b) an alkyl group containing 1 to 3 carbon atoms optionally substituted by one or more halo, c) an alkoxy group containing 1 to 3 carbon atoms optionally substituted by one or more halo, d) an alkylthio group, an alkylsulphinyl group or an alkylsulphonyl group each containing 1 to 3 carbon atoms optionally substituted by one or more halo, e) hydroxy, f) an acyloxy group containing 1 to 3 carbon atoms, g) a hydroxyalkyl group containing 1 to 3 carbon atoms, h) cyano, i) an alkanoyl group containing 1 to 6 carbon atoms, j) an alkoxycarbonyl group containing 2 to 6 carbon atoms, k) a carbamoyl group or a carbamoylmethyl group each optionally N-substituted by one or two alkyl groups each containing 1 to 3 carbon atoms, l) a sulphamoyl or sulphamoylmethyl group each optionally N-substituted by one or two alkyl groups each containing 1 to 3 carbon atoms, or m) an amino group optionally substituted by one or two alkyl groups each containing 1 to 3 carbon atoms; and A represents an alkylene chain containing 1 to 6 carbon atoms each of which may be optionally substituted by one or two alkyl groups each containing 1 to 3 carbon atoms; with the proviso that when HET is a group of formula d), X is S, Ar is phenyl, A is methylene and $R_8$ is pyrid-3-yl, then $R_9$ is other than allyl.

In more preferred compounds of formula I in group 2, HET represents a group of formula d); $R_8$ represents H, an alkyl group containing 1 to 6 carbon atoms optionally substituted by one or more halo, an alkenyl group containing 2 to 6 carbon atoms optionally substituted by one or more halo, or phenyl or a 5 or 6-membered heteroaryl group containing 1 to 3 heteroatoms selected from O, N and S wherein the phenyl or heteroaryl group may be optionally substituted by one or more substituents selected from a) halo, b) an alkyl group containing 1 to 3 carbon atoms optionally substituted by one or more halo, or c) an alkoxy group containing 1 to 3 carbon atoms optionally substituted by one or more halo; $R_9$ represents an alkyl group containing 1 to 3 carbon atoms optionally substituted by one or more halo, an alkenyl group containing 2 to 4 carbon atoms optionally substituted by one or more halo, an alkoxyalkyl group containing 2 to 6 carbon atoms optionally substituted by one or more halo, or pyridyl optionally substituted by one or more substituents selected from a) halo, b) an alkyl group containing 1 to 3 carbon atoms optionally substituted by one or more halo, or c) an alkoxy group containing 1 to 3 carbon atoms optionally substituted by one or more halo; X represents O or S; Ar represents phenyl, pyridyl, pyrimidinyl or 1,4-benzodioxan-5-yl, each of which may be optionally substituted by one or more substituents from a) halo b) an alkyl group containing 1 to 3 carbon atoms optionally substituted by one or more halo, or c) an alkoxy group containing 1 to 3 carbon atoms optionally substituted by one or more halo; and A represents an alkylene chain containing 1 to 6 carbon atoms.

In especially preferred compounds of formula I in group 2, HET represents a group of formula d); $R_8$ represents H, an alkyl group containing 1 to 3 carbon atoms optionally substituted by one or more halo, pyridyl, furyl, thienyl, or phenyl optionally substituted by halo; $R_9$ represents an alkyl group containing 1 to 3 carbon atoms optionally substituted by one or more halo, an alkenyl group containing 2 to 4 carbon atoms optionally substituted by one or more halo, an alkoxyalkyl group containing 2 to 4 carbon atoms optionally substituted by one or more halo, or pyridyl; X represents O or S; Ar represents phenyl, pyridyl, pyrimidinyl or 1,4-benzodioxan-5-yl, each of which may be optionally substituted by one or more substituents selected from a) halo, b) an alkyl group containing 1 to 3 carbon atoms optionally substituted by one or more halo, or c) an alkoxy group containing 1 to 3 carbon atoms optionally substituted by one or more halo; and A represents an alkylene chain containing 1 to 6 carbon atoms. Most preferably, HET is a group of formula d); $R_8$ is H, methyl, trifluoromethyl, pyrid-2-yl, pyrid-3-yl, pyrid-4-yl, 2-furyl, 2-thienyl, phenyl, or 4-chlorophenyl; $R_9$ is allyl, methyl, propyl, 3-methoxypropyl, or pyrid-3-yl; X is O or S; Ar is phenyl, 2-methoxyphenyl, 2-methylphenyl, 2,3-dimethylphenyl, 2-pyrimidinyl, or 1,4-benzodioxan-5-yl; and A is methylene, ethylene, trimethylene or tetramethylene.

In preferred compounds of formula I, Ar represents phenyl, 1,4-benzodioxan-5-yl, pyrimidinyl, naphthyl, benzo[b]furan-7-yl or benzo[b]thiophen-7-yl, each optionally substituted by one or more substituents selected from methyl, trifluoromethyl, an alkoxy group containing 1 to 3 carbon atoms, or halo.

In preferred compounds of formula I, A is an alkylene chain containing 1 to 4 carbon atoms. In more preferred compounds of formula I, A is methylene.

In preferred compounds of formula I, HET is a group of formula a), b) or c). In more preferred compounds of formula I, HET is group of formula a).

In preferred compounds of formula I, $R_1$ is hydroxy, or an amino group optionally substituted by one or two alkyl groups each containing 1 to 3 carbon atoms. In more preferred compounds of formula I, $R_1$ is amino.

In preferred compounds of formula I, $R_2$ and $R_3$ are independently an alkyl group containing 1 to 3 carbon atoms, allyl, or phenyl, pyridyl or pyrimidinyl each optionally substituted by halo or an alkoxy group containing 1 to 3 carbon atoms. In more preferred compounds of formula I, $R_2$ is phenyl and $R_3$ is methyl, propyl or allyl.

In preferred compounds of formula I, $R_4$ is cyclopropyl, cyclobutyl, cyclopentyl, t-butyl, amino or phenyl.

In preferred compounds of formula I, $R_5$ is methyl, t-butyl, benzyl, pyrid-2-yl, pyrid-4-yl, pyrimidin-2-yl, or phenyl optionally substituted by halo, methoxy or cyano.

In preferred compounds of formula I, $R_6$ is methyl.

In preferred compounds of formula I, $R_7$ is H or allyl.

In preferred compounds of formula I, $R_8$ is H, methyl, trifluoromethyl, pyrid-2-yl, pyrid-3-yl, pyrid-4-yl, furan-2-yl, thien-2-yl, or phenyl optionally substituted by halo.

In preferred compounds of formula I, $R_9$ is methyl, propyl, 3-methoxypropyl, allyl or pyrid-3-yl.

In preferred compounds of formula I, Ar' is phenyl or pyrid-3-yl.

It will be understood that any group mentioned herein which contains a chain of three or more atoms signifies a group in which the chain may be straight or branched. For example, an alkyl group may comprise propyl, which includes n-propyl and isopropyl, and butyl, which includes n-butyl, sec-butyl, isobutyl and tert-butyl. The term 'halo' as used herein signifies fluoro, chloro, bromo and iodo.

Compounds of formula I may exist as salts with pharmaceutically acceptable acids. Examples of such salts include hydrochlorides, hydrobromides, sulphates, methanesulphonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

Certain compounds of formula I may exist in more than one physical form (for example different crystal forms) and the present invention includes each physical form (for example each crystal form) of compounds of formula I and mixtures thereof.

Certain compounds of formula I and their salts may exist in more than one crystal form and the present invention includes each crystal form and mixtures thereof. Certain compounds of formula I and their salts may also exist in the form of solvates, for example hydrates, and the present invention includes each solvate and mixtures thereof.

Certain compounds of formula I may contain one or more chiral centres, and exist in different optically active forms. When compounds of formula I contain one chiral centre, the compounds exist in two enantiomeric forms and the present invention includes both enantiomers and mixtures of enantiomers. The enantiomers may be resolved by methods known to those skilled in the art, for example by formation of diastereoisomeric salts which may be separated, for example, by crystallisation; formation of diastereoisomeric derivatives or complexes which may be separated, for example, by crystallisation, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I contains more than one chiral centre it may exist in diastereoisomeric forms. The diastereoisomeric pairs may be separated by methods known to those skilled in the art, for example chromatography or crystallisation and the individual enantiomers within each pair may be separated as described above. The present invention includes each diastereoisomer of compounds of formula I and mixtures thereof.

Specific compounds of formula I are:
3-Amino-4-[4-(2-methoxyphenyl)piperazin-1-ylmethyl]-2-methyl-1-phenyl-3-pyrazolin-5-one;
3-Amino-4-[4-(1,4-benzodioxan-5-yl)piperazin-1-ylmethyl]-2-methyl-1-phenyl-3-pyrazolin-5-one;
3-Amino-2-methyl-4-[4-(2-methylphenyl)piperazin-1-ylmethyl]-1-phenyl-3-pyrazolin-5-one;
3-Amino-2-methyl-4-[4-(1-naphthyl)piperazin-1-ylmethyl]-1-phenyl-3-pyrazolin-5-one;
3-Amino-4-[4-(1,4-benzodioxan-5-yl)piperazin-1-ylmethyl]-1-phenyl-2-propyl-3-pyrazolin-5-one;
2-Allyl-3-amino-4-[4-(1,4-benzodioxan-5-yl)piperazin-1-ylmethyl]-1-phenyl-3-pyrazolin-5-one;
3-Amino-4-[4-(7-benzo[b]furanyl)piperazin-1-ylmethyl]-2-methyl-1-phenyl-3-pyrazolin-5-one;
3-Amino-4-[4-(2-isopropoxyphenyl)piperazin-1-ylmethyl]-2-methyl-1-phenyl-3-pyrazolin-5-one;

5-Amino-3-cyclopropyl-4-[4-(2-methoxyphenyl)piperazin-1-ylmethyl]-1-phenylpyrazole;
5-Amino-4-[4-(1,4-benzodioxan-5-yl)piperazin-1-ylmethyl]-3-cyclopropyl-1-phenylpyrazole;
3,5-Diamino-4-[4-(1,4-benzodioxan-5-yl)piperazin-1-ylmethyl]-1-phenylpyrazole;
5-Amino-4-[4-(1,4-benzodioxan-5-yl)piperazin-1-ylmethyl]-1,3-diphenylpyrazole;
5-Amino-4-[4-(1,4-benzodioxan-5-yl)piperazin-1-ylmethyl]-1-methyl-3-phenylpyrazole;
5-Amino-4-[4-(3-chlorophenyl)piperazin-1-ylmethyl]-3-cyclopropyl-1-phenylpyrazole;
5-Amino-3-cyclopropyl-1-phenyl-4-{4-[3-(trifluoromethyl)phenyl]piperazin-1-ylmethyl}pyrazole;
5-Amino-4-[4-(1,4-benzodioxan-5-yl)piperazin-1-ylmethyl]-3-cyclopropyl-1-(2-pyridyl)pyrazole;
5-Amino-4-[4-(1,4-benzodioxan-5-yl)piperazin-1-ylmethyl]-3-cyclopropyl-1-(4-methoxyphenyl)pyrazole;
5-Amino-3-cyclopropyl-4-[4-(2-methylphenyl)piperazin-1-ylmethyl]-1-phenylpyrazole;
5-Amino-4-[4-(1,4-benzodioxan-5-yl)piperazin-1-ylmethyl]-1-(4-chlorophenyl)-3-cyclopropylpyrazole;
5-Amino-4-[4-(1,4-benzodioxan-5-yl)piperazin-1-ylmethyl]-3-cyclopentyl-1-phenylpyrazole;
5-Amino-4-[4-(1,4-benzodioxan-5-yl)piperazin-1-ylmethyl]-3-tert-butyl-1-phenylpyrazole;
5-Amino-3-cyclopropyl-4-[4-(2-isopropoxyphenyl)piperazin-1-ylmethyl]-1-phenylpyrazole;
5-Amino-4-[4-(1,4-benzodioxan-5-yl)piperazin-1-ylmethyl]-1-tert-butyl-3-cyclopropylpyrazole;
5-Amino-4-[4-(1,4-benzodioxan-5-yl)piperazin-1-ylmethyl]-3-cyclopropyl-1-methylpyrazole;
5-Amino-4-[4-(1,4-benzodioxan-5-yl)piperazin-1-ylmethyl]-1-benzyl-3-cyclopropylpyrazole;
5-Amino-4-[4-(7-benzo[b]furanyl)piperazin-1-ylmethyl]-3-cyclopropyl-1-phenylpyrazole;
5-Amino-3-cyclobutyl-4-[4-(2-isopropoxyphenyl)piperazin-1-ylmethyl]-1-methyl pyrazole;
5-Amino-4-[4-(1,4-benzodioxan-5-yl)piperazin-1-ylmethyl]-3-cyclobutyl-1-phenylpyrazole;
5-Amino-4-[4-(1,4-benzodioxan-5-yl)piperazin-1-ylmethyl]-3-cyclobutyl-1-methylpyrazole;
5-Amino-4-[4-(1,4-benzodioxan-5-yl)piperazin-1-ylmethyl]-3-cyclopentyl-1-methylpyrazole;
4-{5-Amino-4-[4-(1,4-benzodioxan-5-yl)piperazin-1-ylmethyl]-3-cyclopropylpyrazol-1-yl}benzonitrile;
5-Amino-4-[4-(1,4-benzodioxan-5-yl)piperazin-1-ylmethyl]-1-(2-chlorophenyl)-3-cyclopropylpyrazole;
5-Amino-4-[4-(1,4-benzodioxan-5-yl)piperazin-1-ylmethyl]-3-cyclopropyl-1-(4-pyridyl)pyrazole;
5-Amino-4-[4-(1,4-benzodioxan-5-yl)piperazin-1-ylmethyl]-3-cyclopropyl-1-(2-pyrimidinyl)pyrazole;
4-[4-(2-Methoxyphenyl)piperazin-1-ylmethyl]-4-methyl-2-(3-pyridyl)-2-imidazolin-5-one;
4-[4-(2-Methoxyphenyl)piperazin-1-ylmethyl]-4-methyl-2-phenyl-2-imidazolin-5-one;
4-[4-(1,4-Benzodioxan-5-yl)piperazin-1-ylmethyl]-4-methyl-2-phenyl-2-imidazolin-5-one;
1-Allyl-4-[4-(2-methoxyphenyl)piperazin-1-ylmethyl]-4-methyl-2-(3-pyridyl)-2-imidazolin-5-one;
4-[4-(1,4-Benzodioxan-5-yl)piperazin-1-ylmethyl]-4-methyl-2-(3-pyridyl)-2-imidazolin-5-one;
4-Methyl-2-phenyl-4-{4-[3-(trifluoromethyl)phenyl]piperazin-1-ylmethyl}-2-imidazolin-5-one;
4-[4-(3-Chlorophenyl)piperazin-1-ylmethyl]-4-methyl-2-phenyl-2-imidazolin-5-one;
4-Methyl-4-[4-(2-methylphenyl)piperazin-1-ylmethyl]-2-phenyl-2-imidazolin-5-one;
1-Allyl-4-[4-(1,4-benzodioxan-5-yl)piperazin-1-ylmethyl]-4-methyl-2-(3-pyridyl)-2-imidazolin-5-one;
4-Allyl-2-[4-(1,4-benzodioxan-5-yl)piperazin-1-ylmethyl]-5-(3-pyridyl)-1,2,4-triazole-3-(2H,4H)-thione;
4-Allyl-2-{4-[4-(2-methoxyphenyl)piperazin-1-yl]butyl}-5-(3-pyridyl)-1,2,4-triazol-3(2H,4H)-one;
4-Allyl-2-[4-(2-methoxyphenyl)piperazin-1-ylmethyl]-5-(3-pyridyl)-1,2,4-triazole-3(2H,4H)-thione;
5-(4-Chlorophenyl)-2-[4-(2-methoxyphenyl)piperazin-1-ylmethyl]-4-(3-pyridyl)-1,2,4-triazole-3(2H,4H)-thione;
4-Allyl-2-[4-(2-methoxyphenyl)piperazin-1-ylmethyl]-5-(4-pyridyl)-1,2,4-triazole-3(2H,4H)-thione;
2-[4-(2-Methoxyphenyl)piperazin-1-ylmethyl]-4-(3-methoxypropyl)-5-(4-pyridyl)-1,2,4-triazole-3(2H,4H)-thione;
2-[4-(2-Methoxyphenyl)piperazin-1-ylmethyl]-4-methyl-5-(4-pyridyl)-1,2,4-triazole-3(2H,4H)-thione;
4-Allyl-2-[4-(2-methoxyphenyl)piperazin-1-ylmethyl]-5-phenyl-1,2,4-triazole-3(2H,4H)-thione;
2-[4-(2-Methoxyphenyl)piperazin-1-ylmethyl]-4-propyl-5-(4-pyridyl)-1,2,4-triazole-3(2H,4H)-thione;
2-[4-(2-Methoxyphenyl)piperazin-1-ylmethyl]-4-methyl-5-(trifluoromethyl)-1,2,4-triazole-3(2H,4H)-thione;
2-[4-(2-Methoxyphenyl)piperazin-1-ylmethyl]-4-methyl-1,2,4-triazole-3(2H,4H)-thione;
4-Allyl-5-(2-furyl)-2-[4-(2-methoxyphenyl)piperazin-1-ylmethyl]-1,2,4-triazole-3(2H,4H)-thione;
4-Allyl-5-(3-pyridyl)-2-[4-(pyrimidin-2-yl)piperazin-1-ylmethyl]-1,2,4-triazole-3(2H,4H)-thione;
4-Allyl-2-[4-(2-methoxyphenyl)piperazin-1-ylmethyl]-5-(2-pyridyl)-1,2,4-triazole-3(2H,4H)-thione;
4-Allyl-2-[4-(2-methoxyphenyl)piperazin-1-ylmethyl]-5-methyl-1,2,4-triazole-3(2H,4H)-thione;
4-Allyl-2-[4-(2-methoxyphenyl)piperazin-1-ylmethyl]-5-(2-thienyl)-1,2,4-triazole-3(2H,4H)-thione;
4-Allyl-2-[4-(2,3-dimethylphenyl)piperazin-1-ylmethyl]-5-(3-pyridyl)-1,2,4-triazole-3(2H,4H)-thione;
4-Allyl-5-(4-chlorophenyl)-2-[4-(2-methoxyphenyl)piperazin-1-ylmethyl]-1,2,4-triazole-3(2H,4H)-thione;
4-Allyl-2-[4-(2-methoxyphenyl)piperazin-1-ylmethyl]-5-(3-pyridyl)-1,2,4-triazol-3(2H,4H)-one;
4-Allyl-2-{4-[4-(2,3-dimethylphenyl)piperazin-1-yl]butyl}-5-(3-pyridyl)-1,2,4-triazol-3(2H,4H)-one;
4-Allyl-2-{2-[4-(2,3-dimethylphenyl)piperazin-1-yl]ethyl}-5-(3-pyridyl)-1,2,4-triazol-3(2H,4H)-one;
4-Allyl-2-{4-[4-(2-methoxyphenyl)piperazin-1-yl]butyl}-5-phenyl-1,2,4-triazol-3(2H,4H)-one;
4-Allyl-2-{2-[4-(2-methoxyphenyl)piperazin-1-yl]ethyl}-5-phenyl-1,2,4-triazol-3(2H,4H)-one;
4-Allyl-2-{2-[4-(2-methoxyphenyl)piperazin-1-yl]ethyl}-5-(3-pyridyl)-1,2,4-triazol-3(2H,4H)-one;
4-Allyl-2-{2-[4-(2-methoxyphenyl)piperazin-1-yl]ethyl}-5-(2-thienyl)-1,2,4-triazol-3(2H,4H)-one;
4-Allyl-2-{2-[4-(2-methoxyphenyl)piperazin-1-yl]ethyl}-5-methyl-1,2,4-triazol-3(2H,4H)-one;
4-Allyl-2-{2-[4-(2-methylphenyl)piperazin-1-yl]ethyl}-5-(3-pyridyl)-1,2,4-triazol-3(2H,4H)-one;
4-Allyl-2-{3-[4-(2-methoxyphenyl)piperazin-1-yl]propyl}-5-(3-pyridyl)-1,2,4-triazol-3(2H,4H)-one;
and pharmaceutically acceptable salts thereof in the form, where appropriate of individual enantiomers, racemates, or other mixtures of enantiomers.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

The present invention also includes pharmaceutical compositions containing a therapeutically effective amount of a compound of formula I or a salt thereof together with a pharmaceutically acceptable diluent or carrier.

As used hereinafter, the term "active compound" denotes a compound of formula I or a salt thereof. In therapeutic use, the active compound may be administered orally, rectally, parenterally or topically, preferably orally. Thus the therapeutic compositions of the present invention may take the form of any of the known pharmaceutical compositions for oral, rectal, parenteral or topical administration. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are the preferred compositions of the invention and these are the known pharmaceutical forms for such administration, for example tablets, capsules, syrups and aqueous or oil suspensions. The excipients used in the preparation of these compositions are the excipients known in the pharmacist's art. Tablets may be prepared by mixing the active compound with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 1 to 500 mg of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example arachis oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions of the invention suitable for rectal administration are the known pharmaceutical forms for such administration, for example, suppositories with cocoa butter or polyethylene glycol bases.

Pharmaceutical compositions may also be administered parenterally (for example subcutaneously, intramuscularly, intradermally and/or intravenously [such as by injection and/or infusion]) in the known pharmaceutical dosage forms for parenteral administration (for example sterile suspensions in aqueous and/or oily media and/or sterile solutions in suitable solvents, preferably isotonic with the blood of the intended patient). Parenteral dosage forms may be sterilised (for example by micro-filtration and/or using suitable sterilising agents [such as ethylene oxide]). Optionally one or more of the following pharmaceutically acceptable adjuvants suitable for parenteral administration may be added to parenteral dosage forms: local anaesthetics, preservatives, buffering agents and/or mixtures thereof. Parenteral dosage forms may be stored in suitable sterile sealed containers (for example ampoules and/or vials) until use. To enhance stability during storage the parenteral dosage form may be frozen after filling the container and fluid (for example water) may be removed under reduced pressure.

Pharmaceutical compositions may be administered nasally in known pharmaceutical forms for such administration (for example sprays, aerosols, nebulised solutions and/or powders). Metered dose systems known to those skilled in the art (for example aerosols and/or inhalers) may be used.

Pharmaceutical compositions may be administered to the buccal cavity (for example sub-lingually) in known pharmaceutical forms for such administration (for example slow dissolving tablets, chewing gums, troches, lozenges, pastilles, gels, pastes, mouthwashes, rinses and/or powders).

Compositions for topical administration may comprise a matrix in which the pharmacologically active compounds of the present invention are dispersed so that the compounds are held in contact with the skin in order to administer the compounds transdermally. A suitable transdermal composition may be prepared by mixing the pharmaceutically active compound with a topical vehicle, such as a mineral oil, petrolatum and/or a wax, for example paraffin wax or beeswax, together with a potential transdermal accelerant such as dimethyl sulphoxide or propylene glycol. Alternatively the active compounds may be dispersed in a pharmaceutically acceptable cream or ointment base. The amount of active compound contained in a topical formulation should be such that a therapeutically effective amount of the compound is delivered during the period of time for which the topical formulation is intended to be on the skin.

The compounds of the present invention may also be administered by continuous infusion either from an external source, for example by intravenous infusion or from a source of the compound placed within the body. Internal sources include implanted reservoirs containing the compound to be infused which is continuously released for example by osmosis and implants which may be (a) liquid such as a suspension or solution in a pharmaceutically acceptable oil of the compound to be infused for example in the form of a very sparingly water-soluble derivative such as a dodecanoate salt or (b) solid in the form of an implanted support, for example of a synthetic resin or waxy material, for the compound to be infused. The support may be a single body containing all the compound or a series of several bodies each containing part of the compound to be delivered. The amount of active compound present in an internal source should be such that a therapeutically effective amount of the compound is delivered over a long period of time.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients.

The present invention also comprises the use of a compound of formula I as a medicament.

The compounds of formula I or a salt thereof or pharmaceutical compositions containing a therapeutically effective amount thereof may be used in the treatment of depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders, anorexia, cardiovascular and cerebrovascular disorders, non-insulin dependent diabetes mellitus, hyperglycaemia, constipation, arrhythmia, disorders of the neuroendocrine system, stress, prostatic hypertrophy, and spasticity in human beings. Whilst the precise amount of active compound administered in such treatment will depend on a number of factors, for example the age of the patient, the severity of the condition and the past medical history and always lies within the sound discretion of the administering physician, the amount of active compound administered per day is in the range 1 to 1000 mg preferably 5 to 500 mg given in single or divided doses at one or more times during the day.

Preferably, the compounds of formula I or a salt thereof or the pharmaceutical compositions containing a therapeutically effective amount thereof are used in the treatment of depression, anxiety, psychoses (for example schizophrenia), tardive dyskinesia, Parkinson's disease, hypertension, Tourette's syndrome, obsessive-compulsive behaviour, panic attacks, social phobias, cardiovascular and cerebrovascular disorders, stress and prostatic hypertrophy.

A further aspect of the present invention provides the use of a compound of formula I or a salt thereof in the manufacture of a medicament for treating depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy or spasticity in mammals, particularly human beings.

Preferably, the compound of formula I or a salt thereof is used in the manufacture of a medicament for treating depression, anxiety, psychoses (for example schizophrenia), tardive dyskinesia, Parkinson's disease, hypertension, Tourette's syndrome, obsessive-compulsive behaviour, panic attacks, social phobias, cardiovascular and cerebrovascular disorders, stress and prostatic hypertrophy.

The present invention also provides a method of treating depression, anxiety, psychoses (for example schizophrenia), tardive dyskinesia, Parkinson's disease, obesity, hypertension, Tourette's syndrome, sexual dysfunction, drug addiction, drug abuse, cognitive disorders, Alzheimer's disease, senile dementia, obsessive-compulsive behaviour, panic attacks, social phobias, eating disorders and anorexia, cardiovascular and cerebrovascular disorders, non-insulin dependent diabetes mellitus, hyperglycaemia, constipation, arrhythmia, disorders of the neuroendocrine system, stress, prostatic hypertrophy or spasticity which comprises the administration of a therapeutically effective amount of a compound of formula I to a mammal, particularly a human being in need thereof.

Preferably, the method is a method of treating depression, anxiety, psychoses (for example schizophrenia), tardive dyskinesia, Parkinson's disease, hypertension, Tourette's syndrome, obsessive-compulsive behaviour, panic attacks, social phobias, cardiovascular and cerebrovascular disorders, stress and prostatic hypertrophy.

Processes for the preparation of compounds of formula I will now be described. These processes form a further aspect of the present invention. The processes are preferably carried out at atmospheric pressure.

Compounds of formula I in which A is methylene may be prepared by reaction of a compound of formula II

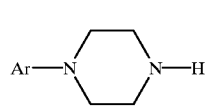

with a compound of formula III

H—HET                                                                III in the presence of formaldehyde in a suitable solvent, for example industrial methylated spirit, at a temperature in the range 0–200° C.; preferably in the range 20–150° C.

Compounds of formula I in which HET represents a group of formula c) wherein $R_7$ is other than H may be prepared by reaction of a compound of formula I in which HET represents a group of formula c) wherein $R_7$ is H, with a compound of formula $R_7Z$ in which Z is a leaving group, for example halo, in the presence of a base, for example potassium hydroxide, at a temperature in the range 0–200° C.; preferably in the range 20–150° C.

Compounds of formula I in which A is an alkylene chain of 2 to 6 carbon atoms and HET is a group of formula d) may be prepared by reaction of a compound of formula IV

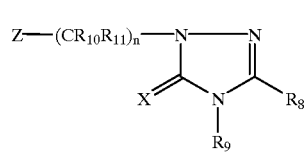

in which Z is a leaving group, for example a halo such as chloro, $R_{10}$ and $R_{11}$ are independently H or an alkyl group containing 1 to 3 carbon atoms and n is 2, 3, 4, 5 or 6 with a compound of formula II in a suitable solvent, for example dimethylformamide, optionally in the presence of a base, for example potassium carbonate, at a temperature in the range 0–200° C.; preferably in the range 20–150° C.

Compounds of formula II may be prepared by reaction of a compound of formula V

Ar—NH$_2$                                                            V with bis(2-chloroethyl)amine in a suitable solvent, for example chlorobenzene, at a temperature in the range 0–200° C.; preferably in the range 20–150° C.

Compounds of formula II may also be prepared by reaction of a compound of formula V with bis(2-hydroxyethyl)amine in the presence of a dehydrating agent, for example phosphorus pentoxide in a suitable solvent, for example diphenyl ether, at a temperature in the range 0–200° C.; preferably in the range 20–150° C.

Compounds of formula II may also be prepared by reaction of a compound of formula VI Ar—Z   VI in which Z is a leaving group, for example a halo such as bromo, with piperazine, optionally in the presence of a solvent, for example water, at a temperature in the range 0–200° C.; preferably in the range 20–150° C.

Compounds of formula II may also be prepared by deprotection of a compound of formula VII

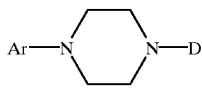

VII in which D is a protecting group, for example tert-butoxycarbonyl, for example by acid hydrolysis in the presence of an acid, for example trifluoroacetic acid, at a temperature in the range 0–150° C.

Certain compounds of formula II are also available commercially.

Compounds of formula III in which HET is a group of formula a) and $R_1$ is $NH_2$ may be prepared by reaction of a compound of formula $R_2NHNHR_3$ with either a compound of formula $NCCH_2CO_2R$ or a compound of formula $ROC(=NH).CH_2CO_2R$ in which R is an alkyl group, for example ethyl, in a suitable solvent, for example ethanol, optionally in the presence of a base, for example sodium ethoxide, at a temperature in the range 0–200° C.; preferably in the range 20–150° C.

Compounds of formula III in which HET is a group of formula a) and $R_1$ is $NH_2$ may also be prepared by reaction of a compound of formula VIII

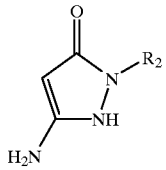

VIII with a compound of formula $R_3Z$, in which Z is a leaving group, for example a halo such as bromo or iodo, in the presence of a base, for example potassium carbonate or sodium hydride, in a suitable solvent, for example acetonitrile or tetrahydrofuran, at a temperature in the range 0–150° C.

Compounds of formula III in which HET is a group of formula a) and $R_1$ is hydroxy may be prepared by reaction of a compound of formula $R_2NHNHR_3$ with a compound of formula $RO_2CCH_2CO_2R$ in which R is an alkyl group, for example ethyl, in a suitable solvent, for example ethanol, optionally in the presence of a base, for example sodium ethoxide, at a temperature in the range 0–200° C.; preferably in the range 20–150° C.

Compounds of formula III in which HET is a group of formula b) in which $R_1$ is $NH_2$ may be prepared by the methods described in Ikuo Adachi et al, Chem. Pharm. Bull., 1987, 35(8), 3235, which involves reaction of a compound of formula $R_4CO.CH_2CN$ with a compound of formula $R_5NHNH_2$ at a temperature in the range 0–200° C., preferably in the range 20–150° C.

Compounds of formula $R_4CO.CH_2CN$ may be prepared by reaction of a compound of formula $R_4CO_2H$ with a coupling agent, for example carbonyl diimidazole, followed by reaction with the dianion of cyanoacetic acid (prepared from cyanoacetic acid which has been pretreated with a base, for example a Grignard reagent such as isopropylmagnesium chloride), in a suitable solvent, for example tetrahydrofuran.

Compounds of formula $R_5NHNH_2$ may be prepared by reaction of a compound of formula $R_5Z$, in which Z is a leaving group, for example a halo such as chloro, with hydrazine hydrate in a suitable solvent, for example ethanol.

Compounds of formula III in which HET is a group of formula c) wherein $R_7$ is H and X is O, may be prepared by reaction of a compound of formula IX

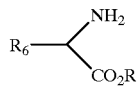

IX in which R is an alkyl group of 1 to 6 carbon atoms, with a compound of formula X

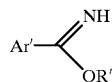

X in which R' is an alkyl group containing 1 to 6 carbon atoms, in a suitable solvent, for example tetrahydrofuran, in the presence of a base, for example triethylamine, at a temperature in the range 0–200° C.; preferably in the range 20–150° C.

Compounds of formula III in which HET is a group of formula d) may be prepared by reaction of a compound of formula $R_9NHCXNHNHCOR_8$ with a base, for example sodium hydroxide, in a suitable solvent, for example water, at a temperature in the range 0–200° C.

Compounds of formula III in which HET is a group of formula d) may also be prepared by reaction of a compound of formula $R_9NHCXNHNH_2$ and a compound of formula $R_8CO_2Et$ in the presence of a base, for example sodium methoxide, in a suitable solvent, for example methanol, at a temperature in the range 0–200° C.

Certain compounds of formula III are also available commercially.

Compounds of formula IV may be prepared by reaction of a compound of formula III in which HET is a group of formula d) with a compound of formula XI $$Z—(CR_{10}R_{11})_n—Z'$$   XI in which Z is a leaving group, for example a halo such as chloro, Z' is a leaving group, for example a halo such as bromo, and n is 2, 3, 4, 5 or 6, in a solvent such as dimethylformamide, in the presence of a base, for example sodium hydride, at a temperature in the range 0–200° C.; preferably in the range 20–150° C.

Compounds of formula VII in which D is a protecting group may be prepared by reaction of a compound of formula VI in which Z is a leaving group, for example a halo such as bromo, with a compound of formula XII

in which D is a protecting group, for example tert-butoxycarbonyl, in the presence of a base, for example sodium tert-butoxide, in a suitable solvent, for example toluene and, in some cases, in the presence of a catalyst, for example that formed by the addition of tri-o-tolylphosphine to bis-(dibenzylideneacetone)palladium (O).

Certain compounds of formula IX are commercially available or may be prepared by methods well known to a person skilled in the art.

Compounds of formula X may be prepared by reaction of a compound of formula XIII Ar'CN                                    XIII with an alcohol of formula R'OH in which R' is an alkyl group containing 1 to 6 carbon atoms, optionally in the presence of an acid or base catalyst, for example sodium methoxide, at a temperature in the range 0–200° C.; preferably in the range 20–150° C.

Compounds of formula $R_9NHCXNHNH_2$ may be prepared by reaction of a compound of formula $H_2NNHCO.R_8$ with a compound of formula $R_9NCX$ in a suitable solvent, for example methanol, at a temperature in the range 0–200° C.; preferably in the range 20–150° C.

The ability of compounds of formula I to interact with 5-hydroxytryptamine (5-HT) receptors has been demonstrated by the following test which determines the ability of the compounds to inhibit tritiated ligand binding to 5-HT receptors in vitro and in particular to $5\text{-}HT_{1A}$ receptors.

Hippocampal tissue from the brains of male Sprague-Dawley rats (Charles River; weight range 150–250 g) was homogenised in ice-cold 50 mM Tris-HCl buffer (pH 7.7 when measured at 25° C., 1:40 w/v) and centrifuged at 30,000 g at 4° C. for 10 minutes. The pellet was rehomogenised in the same buffer, incubated at 37° C. for 10 minutes and centrifuged at 30,000 g at 4° C. for 10 minutes. The final pellet was resuspended in 50 mM Tris-HCl buffer (pH 7.7) containing 4 mM $CaCl_2$, 0.1% L-ascorbic acid and 10 μM pargyline hydrochloride (equivalent to 6.25 mg wet weight of tissue/ml) and used immediately in the binding assay. Aliquots (400 μl; equivalent to 2.5 mg wet weight of tissue/tube) of this suspension were added to tubes containing the ligand (50 μl; 2 nM) and distilled water (50 μl; total binding) or 5-HT (50 μl; 10 μM; non-specific binding) or test compound (50 μl; at a single concentration of $10^{-6}$ M or at 10 concentrations ranging from $10^{-11}$–$10^{-3}$ M). The ligand was [$^3$H]8-hydroxy-2-(dipropylamino)tetralin ([$^3$H]8-OH-DPAT) and the mixture was incubated at 25° C. for 30 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$ M) of test compound. Displacement curves were then produced for those compounds which displaced ≧50% of specific binding of the tritiated ligand at $10^{-6}$ M using a range of concentrations of the compound. The concentration which gave 50% inhibition of specific binding ($IC_{50}$) was obtained from the curve. The inhibition coefficient $K_i$ was then calculated using the formula $$K_i = \frac{IC_{50}}{1 + ([\text{ligand}]/K_D)}$$

in which [ligand] is the concentration of the tritiated ligand used and $K_D$ is the equilibrium dissociation constant for the ligand.

The ability of compounds of formula I to interact with adrenoceptor binding sites has been demonstrated by the following test which determines the ability of the compounds to inhibit tritiated ligand binding to adrenoceptors in vitro and in particular to $\alpha_1$-adrenoceptors.

Whole cortical tissue from the brains of male Charles River CD rats weighing between 150–250 g were homogenised in ice-cold 50 mM Tris-HCl, pH 7.6 (at 25° C.; 1:40 w/v) and centrifuged at 1000 g at 4° C. for 10 minutes. The supernatant was centrifuged at 30,000 g at 4° C. for 10 minutes. The pellet was rehomogenised in 50 mM Tris-HCl, pH 7.6 (1:40 w/v) and centrifuged at 30,000 g at 4° C. for 10 minutes. The final pellet was resuspended in 50 mM Tris-HCl, pH 7.6 (equivalent to 12.5 mg wet weight of tissue/ml) and used immediately in the binding assay. Aliquots (400 μl; equivalent to 5 mg wet weight of tissue/tube) of this suspension were added to tubes containing the ligand (50 μl; 0.1 nM) and distilled water (50 μl; total binding) or phentolamine (50 μl; 5 μM; non-specific binding) or test compound (50 μl; at a single concentration of $10^{-6}$ M or at 10 concentrations ranging from $10^{-11}$–$10^{-3}$ M). The ligand was 7-methoxy-[$^3$H]prazosin and the mixture was incubated at 30° C. for 30 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$ M) of test compound. Displacement curves were then produced for those compounds which displaced ≧50% of specific binding of the tritiated ligand at $10^{-6}$ M using a range of concentrations of the compound. The concentration which gave 50% inhibition of specific binding ($IC_{50}$) was obtained from the curve. The inhibition coefficient $K_i$ was then calculated using the formula $$K_i = \frac{IC_{50}}{1 + ([\text{ligand}]/K_D)}$$

in which [ligand] is the concentration of the tritiated ligand used and $K_D$ is the equilibrium dissociation constant for the ligand.

The ability of compounds of formula I to interact with $\alpha_2$-adrenoceptor binding sites has been demonstrated by the following test which determines the ability of the compounds to inhibit tritiated ligand binding to $\alpha_2$-adrenoceptors in vitro and in particular to $\alpha_{2A}$-adrenoceptors.

Human cerebral cortex obtained at post-mortem was homogenised in ice-cold 0.25M sucrose (1:30 w/v) and centrifuged at 1,000 g at 4° C. for 12 minutes. The supernatant was stored on ice and the pellet was rehomogenised in 0.25M sucrose (1:15 w/v) and centrifuged at 850 g at 4° C. for 12 minutes. Combined supernatants were diluted with 5 mM Tris-HCl (pH 7.5) containing 5 mM ethylenediamine tetraacetic acid (EDTA), readjusted to pH 7.5 (at 25° C.) with 1M sodium hydroxide to 1:80 w/v, and centrifuged at 11,000 g at 4° C. for 10 minutes. The resulting pellet was resuspended in 50 mM Tris-HCl (pH 7.5) containing 5.68 mM L-ascorbic acid and 0.5 mM EDTA, readjusted to pH 7.5 (at 25° C.) with 1M sodium hydroxide to 1:80 w/v, and centrifuged at 11,000 g for 10 minutes. The pellet was stored at −80° C. On the day of the assay the pellet was thawed, resuspended in 50 mM Tris-HCl (pH 7.5) containing 5.68 mM L-ascorbic acid and 5 mM EDTA to 1:80 w/v and centrifuged at 11,000 g for 10 minutes. The final pellet was resuspended in 50 mM Tris-HCl (pH 7.5) containing 5.68 mM L-ascorbic acid and 5 mM EDTA (equivalent to 25 mg wet weight of tissue/ml).

Aliquots (400 µl; equivalent to 10 mg wet weight of tissue/tube) of this suspension were added to tubes containing the ligand (50 µl; 0.2 nM) and distilled water (50 µl; total binding) or phentolamine (50 µl; 50 µM; non-specific binding) or test compound (50 µl; at a single concentration of $10^{-6}$M or at 10 concentrations ranging from $10^{-11}$–$10^{-3}$ M). The ligand was tritiated RX 821002 (2-(2-methoxy-1, 4-[6,7(n)-$^3$H]benzodioxan-2-yl)-2-imidazoline) and the mixture was incubated at 0° C. for 75 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$ M) of test compound. Displacement curves were then produced for those compounds which displaced ≧50% of specific binding of the tritiated ligand at $10^{-6}$ M using a range of concentrations of the compound. The concentration which gave 50% inhibition of specific binding ($IC_{50}$) was obtained from the curve. The inhibition coefficient $K_i$ was then calculated using the formula $$K_i = \frac{IC_{50}}{1 + ([\text{ligand}]/K_D)}$$

in which [ligand] is the concentration of the tritiated ligand used and $K_D$ is the equilibrium dissociation constant for the ligand.

The ability of compounds of formula I to interact with adrenoceptor binding sites has been demonstrated by the following test which determines the ability of the compounds to inhibit tritiated ligand binding to adrenoceptors in vitro and in particular to $\alpha_{2D}$-adrenoceptors.

Frontal cortical tissue from the brains of male Charles River CD rats weighing between 150–250 g were homogenised in ice-cold 0.25 M sucrose (1:30 w/v) and centrifuged at 1,000 g at 4° C. for 12 minutes. The supernatant was stored on ice and the pellet was rehomogenised in 0.25 M sucrose (1:15 w/v) and centrifuged at 850 g at 4° C. for 12 minutes. Combined supernatants were diluted with 5 mM Tris-HCl (pH 7.5) containing 5 mM ethylenediamine tetraacetic acid (EDTA) readjusted to pH 7.5 (at 25° C.) with 1 M sodium hydroxide to 1:80 w/v, and centrifuged at 30,000 g at 4° C. for 10 minutes. The resulting pellet was resuspended in 50 mM Tris-HCl (pH 7.5) containing 5.68 mM L-ascorbic acid and 0.5 mM EDTA readjusted to pH 7.5 (at 25° C.) with 1 M sodium hydroxide, and centrifuged at 30,000 g for 10. minutes. The final pellet was resuspended in 50 mM Tris-HCl (pH 7.5) containing 5.68 mM L-ascorbic acid and 5 mM EDTA (equivalent to 12.5 mg wet weight of tissue/ml) and used immediately in the binding assay. Aliquots (400 µl; equivalent to 5 mg wet weight of tissue/tube) of this suspension were added to tubes containing the ligand (50 µl; 1 nM) and distilled water (50 µl; total binding) or phentolamine (50 µl; 5 µM; non-specific binding) or test compound (50 µl; at a single concentration of $10^{-6}$M or at 10 concentrations ranging from $10^{-11}$–$10^{-3}$ M). The ligand was tritiated idazoxan (2-(1,4-[6,7(n)-$^3$H]benzodioxan-2-yl)-2-imidazoline hydrochloride) and the mixture was incubated at 0° C. for 75 minutes before the incubation was terminated by rapid filtration.

The filters were washed with ice-cold Tris-HCl buffer and dried. The filters were punched out into vials, scintillation fluid added and radioactivity determined by liquid scintillation counting. The percentage displacement of specific binding of the tritiated ligand was calculated for the single concentration ($10^{-6}$M) of test compound. Displacement curves were then produced for those compounds which displaced ≧50% of specific binding of the tritiated ligand at $10^{-6}$ M using a range of concentrations of the compound. The concentration which gave 50% inhibition of specific binding ($IC_{50}$) was obtained from the curve. The inhibition coefficient $K_i$ was then calculated using the formula $$K_i = \frac{IC_{50}}{1 + ([\text{ligand}]/K_D)}$$

in which [ligand] is the concentration of the tritiated ligand used and $K_D$ is the equilibrium dissociation constant for the ligand.

The ability of compounds of formula I to interact with dopamine receptors has been demonstrated by the following test which determines the ability of the compounds to inhibit tritiated ligand binding to dopamine receptors in vitro and in particular to the $D_2$ dopamine receptors.

Striatal tissue from the brains of male Charles River CD rats weighing between 140–250 g were homogenised in ice-cold 50 mM Tris-HCl buffer (pH 7.7 when measured at 25° C.) and centrifuged at 40,000 g for 10 minutes. The pellet was resuspended in Tris salts buffer (50 mM Tris-HCl buffer containing 120 mM NaCl, 5 mM KCl, 2 mM $CaCl_2$ and 1 mM $MgCl_2$ with the addition of 6 mM ascorbic acid; pH 7.7 when measured at 25° C.), and again centrifuged at 40,000 g for 10 minutes. The final pellet was stored at −80° C. Before each test the pellet was resuspended in Tris salts buffer (equivalent to 2 mg wet weight of tissue/ml). Aliquots (720 µl; equivalent to 1.44 mg wet weight of tissue/tube) of this suspension were then added to tubes containing the ligand (40 µl; 1 nM) and Tris salts buffer (40 µl; total binding) or spiroperidol (40 µl; 10 nM; non-specific binding) or test compound (40 µl; at a single concentration of $10^{-6}$M or at 6 concentrations ranging from $10^{-11}$–$10^{-4}$M). The ligand was tritiated (S)-sulpiride and the mixture was incubated at 4° C. for 40 minutes before the incubation was terminated by rapid filtration.

The filters were washed with ice-cold Tris-HCl buffer and dried. The filters were punched out into vials, scintillation fluid added and were left for about 20 hours before being counted by scintillation spectrophotometry. The percentage displacement of specific binding of the tritiated ligand was calculated for the single concentration ($10^{-6}$M) of test compound. Displacement curves were then produced over a range of concentrations for those compounds which displaced ≧50% of specific binding of the tritiated ligand at $10^{-6}$M. The concentration which gave a 50% inhibition of specific binding ($IC_{50}$) was obtained from the curve. The inhibition coefficient $K_i$ was then calculated using the formula $$K_i = \frac{IC_{50}}{1 + ([\text{ligand}]/K_D)}$$

in which [ligand] is the concentration of the tritiated ligand used and $K_D$ is the equilibrium dissociation constant for the ligand.

The $K_i$ values obtained in the above tests for 5-HT$_{1A}$, $\alpha_1$, $\alpha_{2A}$, $\alpha_{2D}$ and D$_2$ binding for each of the final products of Examples 1 to 72 hereinafter are given in Table I below.

TABLE 1

| Example Number | K$_i$ (nM) value for | | | | |
|---|---|---|---|---|---|
| | 5-HT$_{1A}$ | $\alpha_{2A}$ | $\alpha_{2D}$ | $\alpha_1$ | D2 |
| 1 | 169 | NT | 130 | 23 | 192 |
| 2 | 26 | 29 | 307 | 401 | 196 |
| 3 | >500 | 98% | 56% | 89% | >500 |
| 4 | 39 | 82% | >500 | 186 | 112 |
| 5 | 16 | 73% | 121 | 41 | 176 |
| 6 | 22 | 86% | 111 | 45 | 139 |
| 7 | 24 | 91% | 165 | 19 | 177 |
| 8 | 106 | 100% | 21 | 12 | 22 |
| 9 | 49 | NT | 81 | 9 | 374 |
| 10 | 25 | 2 | 162 | 31 | 374 |
| 11 | 16 | 85% | 60 | >500 | 309 |
| 12 | 19 | 99% | 192 | 41 | >500 |
| 13 | 21 | 95% | 156 | 57 | >500 |
| 14 | 74% | 99% | 81% | 80% | >500 |
| 15 | 67% | NT | >500 | >500 | 337 |
| 16 | 4.1 | 100% | 9.7 | 35 | 85 |
| 17 | 59 | 86% | 61 | 27 | >500 |
| 18 | 27 | 98% | 69 | 204 | >500 |
| 19 | 256 | 100% | 4.9 | 38 | >500 |
| 20 | 61 | 89% | 15 | 19 | 445 |
| 21 | 58 | 89% | 32 | 21 | 451 |
| 22 | 29 | 66% | >500 | >500 | >500 |
| 23 | 22 | 100% | 1.7 | 17 | 109 |
| 24 | 21 | 39 | 13 | 177 | 422 |
| 25 | 15 | 14 | 35 | 126 | >500 |
| 26 | 15 | 100% | 8.9 | 9.9 | 185 |
| 27 | 16 | 99% | 4.9 | 7.1 | >500 |
| 28 | 40 | 99% | 93% | 27 | 25 |
| 29 | 34 | 100% | 96% | 50 | >500 |
| 30 | 18 | 99% | 94% | 64 | 265 |
| 31 | 21 | 95% | 82% | 45 | >500 |
| 32 | 129 | 91% | 92% | 44 | 320 |
| 33 | 98% | 100% | 96% | 94% | >500 |
| 34 | 118 | 96% | 87% | 102 | 88 |
| 35 | 2.3 | 100% | 96% | 82 | 184 |
| 36 | 134 | 66% | 127 | 396 | 297 |
| 37 | 93 | 69% | 112 | 271 | 268 |
| 38 | 22 | 196 | 199 | 473 | 281 |
| 39 | 101 | NT | 115 | >500 | 72% |
| 40 | 19 | 69% | 220 | >500 | 315 |
| 41 | 224 | 57% | >500 | >500 | 129 |
| 42 | 213 | 84% | 226 | >500 | >500 |
| 43 | 276 | 93% | 33 | >500 | >500 |
| 44 | 15 | 76% | 54% | >500 | 345 |
| 45 | 31 | NT | 225 | >500 | 322 |
| 46 | 64 | NT | >500 | 16 | 48 |
| 47 | 152 | NT | 178 | >500 | 262 |
| 48 | 108 | NT | 71 | 430 | 200 |
| 49 | 123 | NT | 146 | >500 | 121 |
| 50 | 170 | NT | 194 | >500 | 192 |
| 51 | 54% | NT | >500 | 53% | 134 |
| 52 | 150 | NT | 148 | >500 | 222 |
| 53 | 117 | NT | 150 | >500 | 274 |
| 54 | 135 | NT | 218 | 477 | 243 |
| 55 | 108 | NT | 194 | 358 | 73 |
| 56 | 105 | NT | 197 | 401 | 158 |
| 57 | >500 | NT | 95% | >500 | >500 |
| 58 | 126 | NT | 104 | 301 | 173 |
| 59 | 119 | NT | 255 | 497 | 306 |
| 60 | 138 | NT | 82 | 159 | 155 |
| 61 | 52% | NT | 52% | >500 | >500 |

TABLE 1-continued

| Example Number | K$_i$ (nM) value for | | | | |
|---|---|---|---|---|---|
| | 5-HT$_{1A}$ | $\alpha_{2A}$ | $\alpha_{2D}$ | $\alpha_1$ | D2 |
| 62 | 77% | NT | 68% | 59% | 201 |
| 63 | 74% | NT | 66% | >500 | 193 |
| 64 | 90% | NT | 84% | 98% | 93 |
| 65 | 63% | NT | >500 | 56% | >500 |
| 66 | 92% | NT | >500 | 99% | 169 |
| 67 | 52% | NT | >500 | 78% | >500 |
| 68 | 56% | NT | >500 | 67% | >500 |
| 69 | 70% | NT | >500 | 93% | >500 |
| 70 | 69% | NT | >500 | 64% | 310 |
| 71 | >500 | NT | >500 | 56% | >500 |
| 72 | >500 | NT | >500 | 91% | >500 |

The % figures in Table 1 are for % displacement at 10$^{-6}$M.
NT means Not Tested The invention is illustrated by the following Examples which are given by way of example only. The final product of each of these Examples was characterised by one or more of the following procedures: high performance liquid chromatography; elemental analysis, nuclear magnetic resonance spectroscopy and infrared spectroscopy.

EXAMPLE 1

A mixture of 1-(2-methoxyphenyl)piperazine (2.16 g), 37–40% aqueous formaldehyde solution (0.8 ml) and industrial methylated spirit (27 ml) was stirred at ambient temperature under nitrogen for 18 hours, then a slurry of 3-amino-2-methyl-1-phenyl-3-pyrazolin-5-one (2.14 g) in industrial methylated spirit (54 ml) was added in one portion. The stirred mixture was heated under reflux for 24 hours, allowed to cool to ambient temperature, and the resulting solid was collected by filtration, washed with industrial methylated spirit, and dried in vacuo at 50° C. to give 3-amino-4-[4-(2-methoxyphenyl)piperazin-1-ylmethyl]-2-methyl-1-phenyl-3-pyrazolin-5-one monohydrate as an off-white solid (3.2 g), m.p. 133–136° C.

EXAMPLE 2

A stirred mixture of 2,3-dihydroxybenzoic acid (192.5 g), potassium carbonate (580 g), acetonitrile (950 ml) and water (900 ml) was heated to reflux temperature, then 1,2-dibromoethane (162 ml) was added over 30 minutes. The stirred mixture was heated under reflux for 88 hours, further 1,2-dibromoethane (60 ml) was added, stirring and heating under reflux was continued for 210 hours, further 1,2-dibromoethane (30 ml) and potassium carbonate (100 g) were added, stirring and heating under reflux was continued for 50 hours, further 1,2-dibromoethane (40 ml) was added, and stirring and heating under reflux was continued for 48 hours.

The mixture was combined with that arising from a second reaction performed at the same scale and under the same conditions.

The solvents were removed in vacuo, the residue was dissolved in water (7000 ml), and the solution was washed with ethyl acetate (2×500 ml) and ether (2×500 ml). Charcoal (50 g) was added, and the mixture was stirred at ambient temperature for 30 minutes, then filtered. The filtrate was acidified by the addition of an excess of concentrated hydrochloric acid, and the resulting solid was collected by filtration, washed with water, and dried in vacuo at 95° C. to give 1,4-benzodioxan-5-carboxylic acid as an off-white solid (306.3 g), m.p. 165–173° C.

1,4-Benzodioxan-5-carboxylic acid (120 g) was added in portions at 40° C. to a stirred mixture of hydroxylamine hydrochloride (52 g) and polyphosphoric acid (380 g), then the mixture was heated to an internal temperature of 120° C. The source of heat was removed, and the mixture was stirred vigorously until frothing subsided, then it was stirred at 165° C. for 90 minutes, cooled to 80° C., added to an excess of ice-water, and basified by the addition of 5M aqueous sodium hydroxide solution. The product was extracted into ethyl acetate (6×500 ml), the extracts were dried (MgSO$_4$), and the solvent removed in vacuo. The residue was dissolved in ethyl acetate (800 ml), and the cloudy solution was filtered then saturated with hydrogen chloride. The resulting solid was collected by filtration, washed with ethyl acetate, and dried in vacuo at ambient temperature to give 1,4-benzodioxan-5-amine monohydrochloride as a buff solid (65.9 g).

A stirred mixture of 1,4-benzodioxan-5-amine (21.6 g; prepared by basification of the above hydrochloride salt), bis(2-chloroethyl)amine monohydrochloride (25 g) and chlorobenzene (250 ml) was heated under reflux for 72 hours, then the solvent was removed in vacuo. The residue was diluted with water (250 ml), basified by the addition of 5M aqueous sodium hydroxide solution, and the product was extracted into ethyl acetate (5×100 ml). The extracts were dried (MgSO$_4$), and the solvent removed in vacuo to give 1-(1,4-benzodioxan-5-yl)piperazine as a brown oil (29.2 g).

A mixture of 1-(1,4-benzodioxan-5-yl)piperazine (2.45 g), 37–40% aqueous formaldehyde solution (0.8 ml) and industrial methylated spirit (30 ml) was stirred at ambient temperature under nitrogen for 18 hours, then a slurry of 3-amino-2-methyl-1-phenyl-3-pyrazolin-5-one (1.95 g) in industrial methylated spirit (55 ml) was added in one portion. The stirred mixture was heated under reflux for 5 hours, then allowed to stand at ambient temperature for 18 hours. The resulting solid was collected by filtration, and the filtrate was concentrated in vacuo to 40 ml then cooled in ice to give a second crop of white solid which was collected by filtration. The combined solids were suspended in industrial methylated spirit (80 ml), and the mixture was heated to reflux temperature. Undissolved solid was removed by filtration of the hot mixture, then the filtrate was concentrated to 40 ml, cooled in ice, and the resulting solid was collected by filtration. The two crops of solid were combined and dried in vacuo at 65° C. to give 3-amino-4-[4-(1,4-benzodioxan-5-yl)piperazin-1-ylmethyl]-2-methyl-1-phenyl-3-pyrazolin-5-one 0.75 hydrate as a white solid (2.45 g), m.p. 222–224° C.

EXAMPLE 2

Alternative Preparation

37–40% Aqueous formaldehyde solution (12.4 ml) was added to a solution of 1-(1,4-benzodioxan-5-yl)piperazine (33.1 g; prepared in a similar manner to that described in Example 2 above) in absolute ethanol (250 ml) and the mixture stirred at ambient temperature for 3 hours. The mixture was diluted with absolute ethanol (500 ml) and the resulting solution stirred at ambient temperature for 19 hours. A solution of 3-amino-2-methyl-1-phenyl-3-pyrazolin-5-one (31.7 g) in absolute ethanol (1000 ml) was added and the solution stirred at ambient temperature for 23 hours. The resulting solid was collected by filtration, dried in vacuo at ambient temperature, and suspended in ethyl acetate (1200 ml). The mixture was stirred and heated under reflux for 66 hours, and the resulting solid was collected by hot filtration, dried in vacuo at ambient temperature, ground with a mortar and pestle then again stirred and heated under reflux with ethyl acetate (1700 ml) for 46 hours. The product was collected by hot filtration, then dried in vacuo at ambient temperature to give 3-amino-4-[4-(1,4-benzodioxan-5-yl)piperazin-1-ylmethyl]-2-methyl-1-phenyl-3-pyrazolin-5-one as a white solid (50.4 g), m.p. 223–224° C.

EXAMPLES 3–8

The following compounds of formula I, in which A is methylene and HET is a group of formula a), were prepared by method A below:

| Example No | Name |
| --- | --- |
| 3 | 3-Amino-2-methyl-4-[4-(2-methylphenyl)piperazin-1-ylmethyl]-1-phenyl-3-pyrazolin-5-one |
| 4 | 3-Amino-2-methyl-4-[4-(1-naphthyl)piperazin-1-ylmethyl]-1-phenyl-3-pyrazolin-5-one |
| 5 | 3-Amino-4-[4-(1,4-benzodioxan-5-yl)piperazin-1-ylmethyl]-1-phenyl-2-propyl-3-pyrazolin-5-one |
| 6 | 2-Allyl-3-amino-4-[4-(1,4-benzodioxan-5-yl)piperazin-1-ylmethyl]-1-phenyl-3-pyrazolin-5-one |
| 7 | 3-Amino-4-[4-(7-benzo[b]furanyl)piperazin-1-ylmethyl]-2-methyl-1-phenyl-3-pyrazolin-5-one |
| 8 | 3-Amino-4-[4-(2-isopropoxyphenyl)piperazin-1-ylmethyl]-2-methyl-1-phenyl-3-pyrazolin-5-one |

Method A

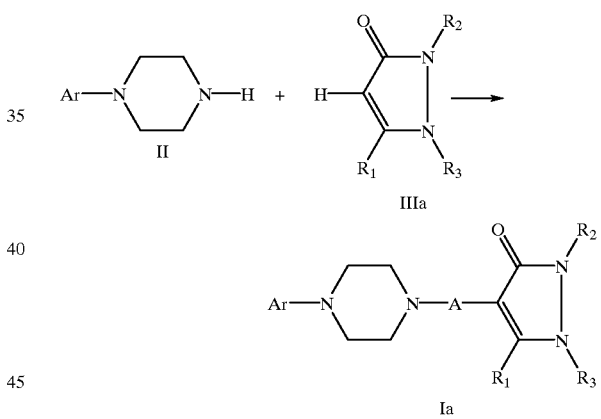

37–40% Aqueous formaldehyde solution (a ml) was added to a solution of a compound of formula II (b g) in industrial methylated spirit (c ml) and the mixture stirred at ambient temperature for d hours under nitrogen. A solution or suspension of a compound of formula IIIa (e g) in industrial methylated spirit (f ml) was added and the mixture was stirred and heated under reflux for g hours. The mixture was allowed to cool to ambient temperature or was cooled in ice. In certain examples the solid product precipitated and was collected by filtration; in others the solvent was removed in vacuo to yield a solid. In some cases the solid was then purified by one or more of the following steps to give a compound of formula Ia with a melting point as given in Table A. Substituents and quantities are also given in Table A.

Purification Steps i) triturated with ethyl acetate then recrystallised from propan-2-ol.

ii) flash column chromatography over silica using 7.5–25% mixtures of methanol in dichloromethane as eluant. The first fraction yielded the desired product which was further purified by dissolving in hot ethyl acetate (100 ml). The solution was allowed to stand at ambient temperature for 16 hours, and the resulting solid was collected by filtration and dried in vacuo to give the desired product.

iii) flash column chromatography over silica using a 3:7 mixture of ethanol and dichloromethane as eluant.

using a 19:1 mixture of dichloromethane and industrial methylated spirit as eluant. Appropriate fractions were combined and the solvents removed in vacuo. The residue was triturated with acetone and the resulting solid was collected by filtration and dried in vacuo at ambient temperature to give 5-amino-3-cyclopropyl-4-[4-(2-methoxyphenyl)

TABLE A

| Ex. No. | Ar | $R_1$ | $R_2$ | $R_3$ | a (ml) | b (g) | c (ml) | d (hr) | e (g) | f (ml) | g (hr) | purif. step | notes | m.p. (° C.) | yield (g) |
|---|---|---|---|---|---|---|---|---|---|---|---|---|---|---|---|
| 3 | 2-Me-phenyl | $NH_2$ | Ph | Me | 0.85 | 1.86 | 10 | 1 | 2 | 70 | 4.75 | i | — | 194–196 | 1.07 |
| 4 | 1-naphthyl | $NH_2$ | Ph | Me | 0.13 | 0.39 | 4 | 16 | 0.35 | 16 | 24 | — | — | 215–220 | 0.16 |
| 5 | 1,4-benzodioxan-5-yl | $NH_2$ | Ph | Pr | 0.96 | 3.05 | 45 | 16 | 3 | 90 | 16 | ii | 1 | 211–214 | 0.56 |
| 6 | 1,4-benzodioxan-5-yl | $NH_2$ | Ph | allyl | 0.40 | 1.26 | 15 | 16 | 1 | 30 | 16 | — | — | 199–201 | 0.70 |
| 7 | benzofuran-7-yl | $NH_2$ | Ph | Me | 0.64 | 1.60 | 20 | 16 | 1.5 | 20 | 1.75 | — | 2 | 199–201 | 1.85 |
| 8 | 2-$OPr^i$-phenyl | $NH_2$ | Ph | Me | 0.38 | 1.05 | 20 | 16 | 0.9 | 20 | 3.5 | iii | 2 | 85–87 | 0.66 |

Notes on Table A
1) Before the solvent was removed in vacuo, the reaction mixture was filtered.
2) The reaction mixture was stirred at ambient temperature, not under reflux conditions.

EXAMPLE 9

A mixture of 1-(2-methoxyphenyl)piperazine (2.4 g), 37–40% aqueous formaldehyde solution (0.9 ml) and industrial methylated spirit (30 ml) was stirred at ambient temperature under nitrogen for 18 hours, then a slurry of 5-amino-3-cyclopropyl-1-phenylpyrazole (2.5 g) in industrial methylated spirit (60 ml) was added in one portion. The stirred mixture was heated under reflux for 24 hours then the solvents were removed in vacuo. The residue was purified by reduced pressure column chromatography over silica piperazin-1-ylmethyl]-1-phenylpyrazole as a white solid (1.4 g), m.p. 70–74° C.

EXAMPLE 10

A mixture of 1-(1,4-benzodioxan-5-yl)piperazine (2.8 g; prepared in a similar manner to that described in Example 2), 37–40% aqueous formaldehyde solution (0.9 ml) and industrial methylated spirit (30 ml) was stirred at ambient temperature under nitrogen for 18 hours then heated under reflux for 30 minutes. A slurry of 5-amino-3-cyclopropyl- 1-phenylpyrazole (2.5 g) in industrial methylated spirit (60 ml) was added in one portion, then the stirred mixture was heated under reflux for 24 hours, and the solvents were removed in vacuo. The residue was purified by reduced pressure column chromatography over silica using a 19:1 mixture of dichloromethane and industrial methylated spirit as eluant. Appropriate fractions were combined, and the solvents removed in vacuo to leave a yellow gum (2.5 g). The gum was dissolved in ether, insoluble material was removed by filtration, and the solvent was removed in vacuo. The residue was triturated with hot petroleum ether (b.p. 60–80° C.) (2×50 ml), the combined petroleum solutions were cooled to ambient temperature, and the resulting solid was collected by filtration and dried in vacuo at ambient temperature to give 5-amino-4-[4-(1,4-benzodioxan-5-yl)piperazin-1-ylmethyl]-3-cyclopropyl-1-phenylpyrazole 0.2 hydrate as a white solid (1.1 g), m.p. 67–70° C.

EXAMPLE 11

Triethylamine (6 ml) was added over 5 minutes to a stirred suspension of diethyl malonimidate dihydrochloride (5 g) in ethanol (50 ml). Phenylhydrazine (2.1 ml) was added, then the mixture was stirred at ambient temperature for 4 hours and at 95° C. for 30 minutes. The solvent was removed in vacuo, and the residue was partitioned between ethyl acetate (100 ml) and water (50 ml). The organic layer was separated, washed with water (50 ml), dried (MgSO$_4$), and the solvent was removed in vacuo. The residue was purified by flash chromatography over silica using a 19:1 mixture of dichloromethane and methanol as eluant, appropriate fractions were combined, and the solvents were removed in vacuo to give 3,5-diamino-1-phenylpyrazole as a red-brown oil (0.76 g).

A mixture of 1-(1,4-benzodioxan-5-yl)piperazine (0.8 g; prepared in a similar manner to that described in Example 2), 37–40% aqueous formaldehyde solution (0.27 ml) and industrial methylated spirit (10 ml) was stirred at ambient temperature under nitrogen for 18 hours, then a solution of 3,5-diamino-1-phenylpyrazole (0.63 g) in industrial methylated spirit (8 ml) was added dropwise. The mixture was stirred at ambient temperature for 2.5 hours, then the solvent was removed in vacuo, and the residue was purified by flash chromatography over silica using an approximately 9:1 mixture of dichloromethane and methanol as eluant. Appropriate fractions were combined and the solvents removed in vacuo to leave 3,5-diamino-4-[4-(1,4-benzodioxan-5-yl)piperazin-1-ylmethyl]-1-phenylpyrazole as a pale pink solid (0.38 g), m.p. 84–87° C.

EXAMPLES 12–35

The following compounds of formula I, in which A is methylene and HET is a group of formula b), were prepared by method B below:

| Example No | Name |
|---|---|
| 12 | 5-Amino-4-[4-(1,4-benzodioxan-5-yl)piperazin-1-ylmethyl]-1,3-diphenylpyrazole |
| 13 | 5-Amino-4-[4-(1,4-benzodioxan-5-yl)piperazin-1-ylmethyl]-1-methyl-3-phenylpyrazole |
| 14 | 5-Amino-4-[4-(3-chlorophenyl)piperazin-1-ylmethyl]-3-cyclopropyl-1-phenylpyrazole |
| 15 | 5-Amino-3-cyclopropyl-1-phenyl-4-{4-[3-(trifluoromethyl)phenyl]piperazin-1-ylmethyl}pyrazole |
| 16 | 5-Amino-4-[4-(1,4-benzodioxan-5-yl)piperazin-1-ylmethyl]-3-cyclopropyl-1-(2-pyridyl)pyrazole |
| 17 | 5-Amino-4-[4-(1,4-benzodioxan-5-yl)piperazin-1-ylmethyl]-3-cyclopropyl-1-(4-methoxyphenyl)pyrazole |
| 18 | 5-Amino-4-[4-(1,4-benzodioxan-5-yl)piperazin-1-ylmethyl]-3-cyclopropyl-1-methylpyrazole 2.3 hydrochloride |
| 19 | 5-Amino-3-cyclopropyl-4-[4-(2-methylphenyl)piperazin-1-ylmethyl]-1-phenylpyrazole |
| 20 | 5-Amino-4-[4-(1,4-benzodioxan-5-yl)piperazin-1-ylmethyl]-1-(4-chlorophenyl)-3-cyclopropylpyrazole |
| 21 | 5-Amino-4-[4-(1,4-benzodioxan-5-yl)piperazin-1-ylmethyl]-3-cyclopentyl-1-phenylpyrazole |
| 22 | 5-Amino-4-[4-(1,4-benzodioxan-5-yl)piperazin-1-ylmethyl]-3-tert-butyl-1-phenylpyrazole |
| 23 | 5-Amino-3-cyclopropyl-4-[4-(2-isopropoxyphenyl)piperazin-1-ylmethyl]-1-phenylpyrazole |
| 24 | 5-Amino-4-[4-(1,4-benzodioxan-5-yl)piperazin-1-ylmethyl]-1-tert-butyl-3-cyclopropylpyrazole |
| 25 | 5-Amino-4-[4-(1,4-benzodioxan-5-yl)piperazin-1-ylmethyl]-3-cyclopropyl-1-methylpyrazole |
| 26 | 5-Amino-4-[4-(1,4-benzodioxan-5-yl)piperazin-1-ylmethyl]-1-benzyl-3-cyclopropylpyrazole |
| 27 | 5-Amino-4-[4-(7-benzo[b]furanyl)piperazin-1-ylmethyl]-3-cyclopropyl-1-phenylpyrazole |
| 28 | 5-Amino-3-cyclobutyl-4-[4-(2-isopropoxyphenyl)piperazin-1-ylmethyl]-1-methylpyrazole |
| 29 | 5-Amino-4-[4-(1,4-benzodioxan-5-yl)piperazin-1-ylmethyl]-3-cyclobutyl-1-phenylpyrazole |
| 30 | 5-Amino-4-[4-(1,4-benzodioxan-5-yl)piperazin-1-ylmethyl]-3-cyclobutyl-1-methylpyrazole |
| 31 | 5-Amino-4-[4-(1,4-benzodioxan-5-yl)piperazin-1-ylmethyl]-3-cyclopentyl-1-methylpyrazole |
| 32 | 4-{5-Amino-4-[4-(1,4-benzodioxan-5-yl)piperazin-1-ylmethyl]-3-cyclopropylpyrazol-1-yl}benzonitrile |
| 33 | 5-Amino-4-[4-(1,4-benzodioxan-5-yl)piperazin-1-ylmethyl]-1-(2-chlorophenyl)-3-cyclopropylpyrazole |
| 34 | 5-Amino-4-[4-(1,4-benzodioxan-5-yl)piperazin-1-ylmethyl]-3-cyclopropyl-1-(4-pyridyl)pyrazole |
| 35 | 5-Amino-4-[4-(1,4-benzodioxan-5-yl)piperazin-1-ylmethyl]-3-cyclopropyl-1-(2-pyrimidinyl)pyrazole |

Method B

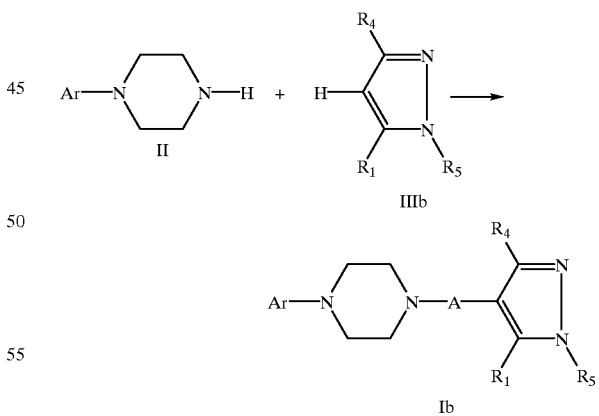

37–40% Aqueous formaldehyde solution (a ml) was added to a solution of a compound of formula II (b g) in industrial methylated spirit (c ml) and the mixture stirred at ambient temperature for d hours under nitrogen. A solution or suspension of a compound of formula IIIb (e g) in industrial methylated spirit (f ml) was added and the mixture was stirred and heated under reflux for g hours. The mixture was allowed to cool to ambient temperature and the solvent was removed in vacuo to yield the crude product. In some cases the product was then purified by one or more of the following steps to give a compound of formula Ib with a melting point as given in Table B. Substituents and quantities are also given in Table B.

Purification Steps i) reduced pressure column chromatography over silica using a 19:1 mixture of dichloromethane and industrial methylated spirit as eluant. Appropriate fractions were combined, the solvents were removed in vacuo, the residue was dissolved in ether and a solution of maleic acid (2 g) in ether (200 ml) was added. The resulting solid was collected by filtration, dried in vacuo and then dissolved in a mixture of ethyl acetate and water. The solution was basified, and the free base extracted into ethyl acetate. The extracts were dried ($MgSO_4$) and the solvent removed in vacuo. The resulting oil was further purified by reduced pressure column chromatography using a 1:1 mixture of ethyl acetate and petroleum ether (b.p. 60–80° C.) to yield the desired product.

ii) reduced pressure column chromatography over silica using a 12:1 mixture of dichloromethane and industrial methylated spirit as eluant. Appropriate fractions were combined, the solvents were removed in vacuo, the residue was dissolved in ether and a solution of maleic acid (2 g) in ether (200 ml) was added. The resulting solid was collected by filtration, dried in vacuo and then dissolved in water. The solution was basified and the free base was extracted into ether. The extracts were dried ($MgSO_4$) and the solvent removed in vacuo. The residue was further purified by reduced pressure column chromatography over silica using a 19:1 mixture of dichloromethane and industrial methylated spirit as eluant. The resulting solid was dissolved in a mixture of ether and petroleum ether (b.p. 40–60° C.), and the solvent allowed to evaporate to yield the desired product.

iii) The crude product was redissolved in acetone, and the solution was filtered, then diluted with 5 volumes of petroleum ether (b.p. 60–80° C.). The solvents were allowed to concentrate to 100 ml at ambient temperature. The supernatant liquors were decanted and the residue was triturated with acetone. The undissolved solid was collected by filtration to yield the desired product.

iv) The crude product was purified by column chromatography over silica using a 19:1 mixture of dichloromethane and industrial methylated spirit as eluant, then recrystallised from a 1:10 mixture of ether and petroleum ether (b.p. 60–80° C.) to give the desired product.

v) flash column chromatography over silica using a 1:99 mixture of industrial methylated spirit and dichloromethane as eluant.

vi) flash column chromatography over silica using a 1:19 mixture of industrial methylated spirit and dichloromethane as eluant.

vii) reduced pressure column chromatography over silica using a 9:1 mixture of dichloromethane and industrial methylated spirit as eluant. Appropriate fractions were combined and the solvents removed in vacuo. The residue was dissolved in ether and hydrogen chloride gas passed through the solution. The resulting solid was collected by filtration, dried in vacuo, triturated with ethyl acetate and dried in vacuo at 70° C. to give the desired product.

viii) flash column chromatography over silica; first using 5–10% mixtures of methanol in dichloromethane as eluant, then a second purification using 30–40% mixtures of ethyl acetate in petroleum ether (b.p. 60–80° C.).

ix) The crude product was purified by column chromatography over silica using a 19:1 mixture of dichloromethane and industrial methylated spirit as eluant, then triturated with petroleum ether (b.p. 60–80° C.) to give the desired product.

x) flash column chromatography over silica; first using 1–5% mixtures of methanol in dichloromethane as eluant, then a second purification using 30–50% mixtures of ethyl acetate in petroleum ether (b.p. 60–80° C.), then a third purification using 25–40% mixtures of ethyl acetate in petroleum ether (b.p. 60–80° C.).

xi) The crude product was purified by flash column chromatography over silica using a 1:1 mixture of ethanol and dichloromethane as eluant.

xii) flash column chromatography over silica using a 19:1 mixture of dichloromethane and methanol as eluant. The resulting gum was dissolved in ether (100 ml), and the solvent was removed in vacuo to give the desired product.

xiii) Half of the crude product was purified by reduced pressure column chromatography over silica using a 9:1 mixture of dichloromethane and industrial methylated spirit as eluant. The appropriate fractions were combined, the solvents removed in vacuo, and the residue triturated with petroleum ether (b.p. 60–80° C.) followed by ether to give the desired product.

xiv) The oil obtained after column chromatography was dissolved in ethyl acetate, ether was added and the resulting solid was the desired product.

xv) flash column chromatography over silica using a 1:1 mixture of ethyl acetate and petroleum ether (b.p. 60–80° C.) as eluant.

xvi) flash column chromatography over silica using a 95:5 mixture of ether and methanol as eluant.

xvii) flash column chromatography over silica; first using a 95:5 mixture of dichloromethane and methanol, then a second purification using a 96:4 mixture of dichloromethane and industrial methylated spirit as eluant.

xviii) flash column chromatography over silica using a 3:97 mixture of methanol and dichloromethane as eluant.

xix) flash column chromatography over silica using a 19:1 mixture of dichloromethane and methanol as eluant. The resulting semisolid was triturated with ether, then the solvent was removed in vacuo to give the desired product.

xx) flash column chromatography over silica using 2–5% mixtures of industrial methylated spirit in dichloromethane as eluant. The resulting oil was dissolved in ether and the solvent removed in vacuo to give the desired product.

xxi) flash column chromatography over silica using a 7% mixture of methanol in ethyl acetate as eluant, then a second purification using a 10% mixture of methanol in ethyl acetate.

xxii) flash column chromatography over silica using a 10% mixture of methanol in ethyl acetate as eluant.

TABLE B

| Ex. No. | Ar | R₁ | R₄ | R₅ | a (ml) | b (g) | c (ml) | d (hr) | e (g) | f (ml) | g (hr) | purif. step | notes | m.p. (° C.) | yield (g) |
|---|---|---|---|---|---|---|---|---|---|---|---|---|---|---|---|
| 12 | 5-methyl-2,3-dihydro-1,4-benzodioxine | NH₂ | Ph | Ph | 1.0 | 3.1 | 25 | 20 | 3.3 | 100 | 48 | i | — | 86–92 | 0.6 |
| 13 | 5-methyl-2,3-dihydro-1,4-benzodioxine | NH₂ | Ph | Me | 1.0 | 3.1 | 25 | 20 | 2.4 | 100 | 24 | ii | — | 80–90 | 0.4 |
| 14 | 3-chlorophenyl | NH₂ | cyclopropyl | Ph | 0.9 | 2.5 | 30 | 16 | 2.5 | 60 | 72 | iii | — | 128–132 | 1.44 |
| 15 | 3-(trifluoromethyl)phenyl | NH₂ | cyclopropyl | Ph | 0.9 | 2.92 | 30 | 16 | 2.5 | 60 | 72 | iv | — | 67–70 | 1.67 |
| 16 | 5-methyl-2,3-dihydro-1,4-benzodioxine | NH₂ | cyclopropyl | 2-pyridyl | 0.66 | 1.93 | 20 | 16 | 1.96 | 20 | 5 | v | 1 | 73–75 | 0.23 |

TABLE B-continued

| Ex. No. | Ar | $R_1$ | $R_4$ | $R_5$ | a (ml) | b (g) | c (ml) | d (hr) | e (g) | f (ml) | g (hr) | purif. step | notes | m.p. (° C.) | yield (g) |
|---|---|---|---|---|---|---|---|---|---|---|---|---|---|---|---|
| 17 | 5-methyl-2,3-dihydrobenzo[1,4]dioxine | $NH_2$ | cyclopropyl | 4-OMe-phenyl | 0.55 | 1.68 | 30 | 16 | 1.75 | 15 | 3 | vi | 2 | 70–72 | 1.9 |
| 18 | 5-methyl-2,3-dihydrobenzo[1,4]dioxine | $NH_2$ | cyclopropyl | Me | 1.80 | 5.4 | 15 | 18 | 3.35 | 60 | 20 | vii | — | 115–130 | 0.7 |
| 19 | 2-methylphenyl | $NH_2$ | cyclopropyl | Ph | 1.0 | 2.47 | 30 | 16 | 2.8 | 60 | 24 | ix | — | oil. | 2.0 |
| 20 | 5-methyl-2,3-dihydrobenzo[1,4]dioxine | $NH_2$ | cyclopropyl | 4-Cl-phenyl | 0.47 | 1.51 | 30 | 16 | 1.6 | 15 | 3 | vi | 2 | 76–78 | 2.05 |
| 21 | 5-methyl-2,3-dihydrobenzo[1,4]dioxine | $NH_2$ | cyclopentyl | Ph | 0.51 | 1.64 | 75 | 16 | 1.79 | 75 | 4 | viii | 2 | 72–82 | 0.97 |

TABLE B-continued

| Ex. No. | Ar | $R_1$ | $R_4$ | $R_5$ | a (ml) | b (g) | c (ml) | d (hr) | e (g) | f (ml) | g (hr) | purif. step | notes | m.p. (° C.) | yield (g) |
|---|---|---|---|---|---|---|---|---|---|---|---|---|---|---|---|
| 22 | 5-methyl-2,3-dihydro-1,4-benzodioxin | $NH_2$ | $Bu^t$ | Ph | 0.9 | 3.06 | 40 | 16 | 2 | 40 | 5 | x | 2 | 88 | 0.6 |
| 23 | 2-methyl-phenyl-$OPr^i$ | $NH_2$ | cyclopropyl | Ph | 0.4 | 1.15 | 0 | 0.5 | 1.03 | 75 | 24 | xi | 2 | 55–60 | 0.5 |
| 24 | 5-methyl-2,3-dihydro-1,4-benzodioxin | $NH_2$ | cyclopropyl | $Bu^t$ | 1.35 | 4.3 | 40 | 18 | 3.5 | 40 | 24 | xii | 2 | 128–131 | 4.23 |
| 25 | 5-methyl-2,3-dihydro-1,4-benzodioxin | $NH_2$ | cyclopropyl | Me | 6.0 | 17.5 | 80 | 16 | 10.9 | 150 | 4 | xiii | 2 | 80–85 | 3.1 |
| 26 | 5-methyl-2,3-dihydro-1,4-benzodioxin | $NH_2$ | cyclopropyl | —$CH_2Ph$ | 0.7 | 2.0 | 10 | 18 | 1.9 | 20 | 4 | vi, xiv | 2 | 130–132 | 0.1 |

TABLE B-continued

| Ex. No. | Ar | $R_1$ | $R_4$ | $R_5$ | a (ml) | b (g) | c (ml) | d (hr) | e (g) | f (ml) | g (hr) | purif. step | notes | m.p. (° C.) | yield (g) |
|---|---|---|---|---|---|---|---|---|---|---|---|---|---|---|---|
| 27 | 7-methylbenzofuran | $NH_2$ | cyclopropyl | Ph | 0.32 | 0.85 | 20 | 16 | 0.84 | 10 | 3 | xv | 2 | 64–66 | 0.99 |
| 28 | 2-methyl-$OPr^i$-phenyl | $NH_2$ | cyclobutyl | Me | 0.39 | 0.95 | 20 | 16 | 0.65 | 10 | 6 | xvi | 2 | 126–129 | 0.63 |
| 29 | 5-methyl-2,3-dihydrobenzo[1,4]dioxine | $NH_2$ | cyclobutyl | Ph | 0.34 | 0.92 | 15 | 16 | 0.89 | 15 | 6 | xv | 2 | 66–68 | 1.10 |
| 30 | 5-methyl-2,3-dihydrobenzo[1,4]dioxine | $NH_2$ | cyclobutyl | Me | 0.75 | 2.0 | 20 | 16 | 1.37 | 10 | 8 | xvii | 2 | 76–78 | 0.91 |
| 31 | 5-methyl-2,3-dihydrobenzo[1,4]dioxine | $NH_2$ | cyclopentyl | Me | 0.98 | 2.67 | 25 | 16 | 2.0 | 25 | 6 | xviii | 2 | 64–66 | 3.8 |

TABLE B-continued

| Ex. No. | Ar | $R_1$ | $R_4$ | $R_5$ | a (ml) | b (g) | c (ml) | d (hr) | e (g) | f (ml) | g (hr) | purif. step | notes | m.p. (° C.) | yield (g) |
|---|---|---|---|---|---|---|---|---|---|---|---|---|---|---|---|
| 32 | 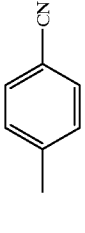 | $NH_2$ | cyclopropyl | 4-CN-phenyl | 0.31 | 0.98 | 10 | 16 | 1.0 | 50 | 24 | xix | 2 | 101–103 | 1.01 |
| 33 | 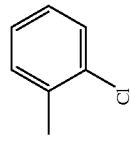 | $NH_2$ | cyclopropyl | 2-Cl-phenyl | 0.92 | 2.83 | 50 | 16 | 3.0 | 25 | 72 | xx | 2 | 78 | 4.47 |
| 34 | 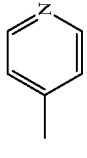 | $NH_2$ | cyclopropyl | 4-pyridyl | 0.69 | 1.73 | 25 | 16 | 1.57 | 25 | 16 | xxi | 2 | 82–84 | 0.87 |
| 35 | 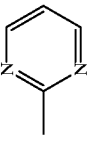 | $NH_2$ | cyclopropyl | 2-pyridyl | 0.54 | 1.56 | 15 | 16 | 1.43 | 40 | 16 | xxii | 2 | 71–73 | 2.07 |

Notes on Table B
1) Before the solvent was removed in vacuo, a solid precipitate was removed by filtration.
2) The reaction mixture was stirred at ambient temperature, not under reflux conditions.

EXAMPLE 36

A solution of nicotinonitrile (11.35 g) and sodium methoxide (1.1 g) in methanol was allowed to stand at ambient temperature under nitrogen for 18 hours, then acetic acid (1.2 ml) was added, and the solvent was removed in vacuo. The residue was triturated with cyclohexane, undissolved solid was removed by filtration, and the solvent was removed in vacuo to leave methyl pyridine-3-carboximidate as an orange oil (10.6 g).

A stirred mixture of methyl pyridine-3-carboximidate (10.6 g), alanine ethyl ester monohydrochloride (10 g), triethylamine (8.4 ml) and tetrahydrofuran (250 ml) was heated under reflux under nitrogen for 5 hours then allowed to cool to ambient temperature. The resulting solid was collected by filtration and washed with tetrahydrofuran. The filtrate and washings were combined and the solvent removed in vacuo. The residue was triturated with a 1:1 mixture of ether and ethyl acetate, and the resulting solid was collected by filtration and washed with ether. The two crops of solid were combined, suspended in water (130 ml), and the mixture was stirred at ambient temperature for 1 hour. The resulting solid was collected by filtration and dried in vacuo to give 4-methyl-2-(3-pyridyl)-2-imidazolin-5-one as a yellow solid (4.9 g), m.p. 238–241° C.

A mixture of 1-(2-methoxyphenyl)piperazine (1.65 g) and 37–40% aqueous formaldehyde solution (0.39 ml) was stirred at ambient temperature under nitrogen for 10 minutes, then a suspension of 4-methyl-2-(3-pyridyl)-2-imidazolin-5-one (1.5 g) in industrial methylated spirit (75 ml) was added in one portion. The mixture was stirred and heated under reflux for 52 hours, then the solvent was removed in vacuo. The residue was triturated with a 49:49:2 mixture of ether, ethyl acetate and propan-2-ol, and the resulting solid was collected by filtration, washed with ethyl acetate, and dried in vacuo at ambient temperature to give 4-[4-(2-methoxyphenyl)piperazin-1-ylmethyl]-4-methyl-2-(3-pyridyl)-2-imidazolin-5-one as an off-white solid (1.55 g), m.p. 159–162° C.

EXAMPLE 37

A mixture of methyl benzimidate monohydrochloride (5 g), alanine ethyl ester monohydrochloride (4.77 g), triethylamine (8.5 ml) and tetrahydrofuran (130 ml) was stirred and heated under reflux under nitrogen for 5.5 hours, then the solvent was removed in vacuo. The residue was triturated with a 1:1 mixture of ether and ethyl acetate, and the resulting yellow solid was collected by filtration and suspended in water (100 ml). The mixture was stirred at ambient temperature for 1 hour, then the resulting solid was collected by filtration, and dried in vacuo to give 4-methyl-2-phenyl-2-imidazolin-5-one as a yellow solid (2.58 g), m.p. 165° C.

A mixture of 1-(2-methoxyphenyl)piperazine (2.4 g) and 37–40% aqueous formaldehyde solution was stirred at ambient temperature under nitrogen for 10 minutes, then a suspension of 4-methyl-2-phenyl-2-imidazolin-5-one (2.58 g) in industrial methylated spirit (100 ml) was added in one portion. The stirred mixture was heated under reflux for 48 hours, then the solvent was removed in vacuo. The residue was triturated with a 2:1 mixture of cyclohexane and ether, undissolved solid was removed by filtration, then the filtrate was allowed to concentrate at ambient temperature. The resulting solid was collected by filtration. Further concentration of the filtrate yielded a second crop of solid. The two crops of solid were combined and dried in vacuo at ambient temperature to give 4-[4-(2-methoxyphenyl)piperazin-1-ylmethyl]-4-methyl-2-phenyl-2-imidazolin-5-one 1.1 hydrate as a colourless solid (0.2 g), m.p. 86–89° C.

EXAMPLE 38

A mixture of 1-(1,4-benzodioxan-5-yl)piperazine (4.96 g; prepared in a similar manner to that described in Example 2), 37–40% aqueous formaldehyde solution (1 ml) and industrial methylated spirit (40 ml) was stirred at ambient temperature under nitrogen for 30 minutes, then a suspension of 4-methyl-2-phenyl-2-imidazolin-5-one (3.82 g; prepared in a similar manner to that described in Example 37) in industrial methylated spirit (100 ml) was added in one portion. The mixture was stirred and heated under reflux for 18 hours, then the solvent was removed in vacuo. The residue was purified by flash chromatography over silica using a 1:1 mixture of ethyl acetate and ethanol as eluant. Appropriate fractions were combined and the solvents removed in vacuo to leave an oil. The oil was triturated with ethyl acetate, undissolved solid was removed by filtration, the filtrate was diluted with cyclohexane, and the resulting solid was collected by filtration and dried in vacuo at ambient temperature to give 4-[4-(1,4-benzodioxan-5-yl)piperazin-1-ylmethyl]-4-methyl-2-phenyl-2-imidazolin-5-one 1.1 hydrate as an off-white solid (0.6 g), m.p. 80–85° C.

EXAMPLE 39

A mixture of 4-[4-(2-methoxyphenyl)piperazin-1-ylmethyl]-4-methyl-2-(3-pyridyl)-2-imidazolin-5-one (3.7 g; prepared in a similar manner to that described in Example 36), allyl bromide (1.05 ml), finely-powdered potassium hydroxide (0.79 g), 18-Crown-6 (0.26 g) and tetrahydrofuran (50 ml) was stirred at ambient temperature under nitrogen for 120 hours, then poured onto ice-water (30 ml). The product was extracted into ethyl acetate, the extracts were dried (MgSO$_4$), and the solvent was removed in vacuo. The residue was purified by flash chromatography over silica using a 9:1 mixture of ethyl acetate and ethanol as eluant. Appropriate fractions were combined, and the solvents removed in vacuo to leave 1-allyl-4-[4-(2-methoxyphenyl)piperazin-1-ylmethyl]-4-methyl-2-(3-pyridyl)-2-imidazolin-5-one as an off-white solid (0.25 g), m.p. 66–69° C.

EXAMPLES 40–43

The following compounds of formula I, in which A is methylene and HET is a group of formula c), were prepared by method C below:

| Example No. | Name |
|---|---|
| 40 | 4-[4-(1,4-Benzodioxan-5-yl)piperazin-1-ylmethyl]-4-methyl-2-(3-pyridyl)-2-imidazolin-5-one |
| 41 | 4-Methyl-2-phenyl-4-{4-[3-(trifluoromethyl)phenyl]piperazin-1-ylmethyl}-2-imidazolin-5-one |

-continued

| Example No. | Name |
|---|---|
| 42 | 4-[4-(3-Chlorophenyl)piperazin-1-ylmethyl]-4-methyl-2-phenyl-2-imidazolin-5-one |
| 43 | 4-Methyl-4-[4-(2-methylphenyl)piperazin-1-ylmethyl]-2-phenyl-2-imidazolin-5-one |

Method C

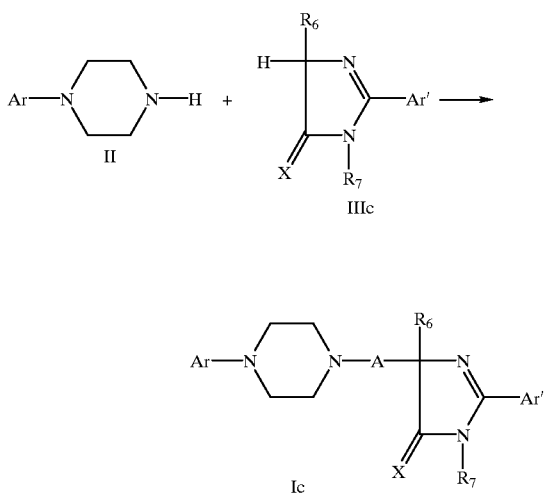

37–40% Aqueous formaldehyde solution (a ml) was added to a solution of a compound of formula II (b g) in industrial methylated spirit (c ml) and the mixture stirred at ambient temperature for d hours under nitrogen. A solution or suspension of a compound of formula IIIc (e g) in industrial methylated spirit (f ml) was added and the mixture was stirred and heated under reflux for g hours. The mixture was allowed to cool to ambient temperature and the solvent was removed in vacuo to yield the crude product. In some cases the product was then purified by one or more of the following steps to give a compound of formula Ic with a melting point as given in Table C. Substituents and quantities are also given in Table C.

Purification Steps i) flash column chromatography over silica using a 4:1 mixture of ethyl acetate and dichloromethane as eluant.

ii) trituration with ether.

iii) flash column chromatography over silica using a 9:1 mixture of dichloromethane and industrial methylated spirit as eluant.

iv) trituration with petroleum ether (b.p. 40–60° C.).

v) dissolved in ethyl acetate, the solution filtered, and the solvent removed in vacuo.

vi) dissolved in ether, the solution filtered, and the solvent removed in vacuo.

vii) recrystallised from propan-2-ol.

viii) all liquors were combined and the solvents removed in vacuo.

ix) extracted into hot petroleum ether (b.p. 80–100° C.), allowed to cool, and the solid which formed was collected by filtration.

TABLE C

| Ex. No | Ar | X | Ar' | $R_6$ | $R_7$ | a (ml) | b (g) | c (ml) | d (hr) | e (g) | f (ml) | g (hr) | purif. step | NB | m.p. (° C.) | yield (g) |
|---|---|---|---|---|---|---|---|---|---|---|---|---|---|---|---|---|
| 40 | benzodioxine | O | pyridyl | Me | H | 5.25 | 26.4 | 25 | 1 | 21.04 | 250 | 20 | i, ii | — | 121 | 3.7 |
| 41 | 3-CF₃-phenyl | O | Ph | Me | H | 1.0 | 2.31 | 20 | 18 | 1.73 | 80 | 18 | iii, iv | — | 153–156 | 0.9 |

TABLE C-continued

| Ex. No | Ar | X | Ar' | R₆ | R₇ | a (ml) | b (g) | c (ml) | d (hr) | e (g) | f (ml) | g (hr) | purif. step | NB | m.p. (° C.) | yield (g) |
|---|---|---|---|---|---|---|---|---|---|---|---|---|---|---|---|---|
| 42 | 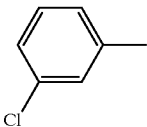 | O | Ph | Me | H | 1.0 | 1.97 | 15 | 16 | 1.73 | 80 | 18 | v, vi, iv, ii | — | 163–165 | 1.0 |
| 43 | 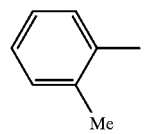 | O | Ph | Me | H | 1.0 | 1.76 | 10 | 16 | 1.73 | 80 | 2 | vi, iv, ii, vii, viii, iv, ix | 1 | 119–121 | 1.0 |

Notes to Table C
1) The reaction mixture was stirred at ambient temperature, not under reflux conditions

EXAMPLE 44

A solution of allyl bromide (0.7 ml) in dry tetrahydrofuran (5 ml) was added dropwise at 0° C. under nitrogen to a stirred mixture of 4-[4-(1,4-benzodioxan-5-yl)piperazin-1-ylmethyl]-4-methyl-2-(3-pyridyl)-2-imidazolin-5-one (2.86 g; prepared in a similar manner to that described in Example 40), powdered potassium hydroxide (0.57 g) and 18-Crown-6 (0.18 g) in dry tetrahydrofuran (60 ml). The mixture was stirred at ambient temperature for 17 hours then poured onto ice-water (30 ml) and the product extracted into ether. The extracts were dried (MgSO₄) and the solvents removed in vacuo to yield a foam which was triturated with ether. The precipitate was collected by filtration to yield 1-allyl-4-[4-(1,4-benzodioxan-5-yl)piperazin-1-ylmethyl]-4-methyl-2-(3-pyridyl)-2-imidazolin-5-one as a solid (0.53 g), m.p. 102–105° C.

EXAMPLE 45

A mixture of 1-(1,4-benzodioxan-5-yl)piperazine (1 g; prepared in a similar manner to that described in Example 2), 4-allyl-5-(3-pyridyl)-1,2,4-triazole-3(2H,4H)-thione (1 g), 37–40% aqueous formaldehyde solution (0.5 ml) and t-butanol (60 ml) was stirred at ambient temperature for 30 minutes, heated under reflux for 15 minutes, then the solvent was removed in vacuo. The residue was triturated with a 1:1 mixture of cyclohexane and ether (40 ml), and the resulting solid was collected by filtration and dried in vacuo at ambient temperature to give 4-allyl-2-[4-(1,4-benzodioxan-5-yl)piperazin-1-ylmethyl]-5-(3-pyridyl)-1,2,4-triazole-3(2H,4H)-thione as a white solid (0.62 g), m.p. 122–127° C.

EXAMPLE 46

Allyl isocyanate (16.8 g) was added dropwise at ambient temperature to a stirred suspension of nicotinic hydrazide (25 g) in methanol (500 ml), then the mixture was stirred at ambient temperature for 2.75 hours, concentrated in vacuo to 250 ml, then diluted with ether (750 ml). The resulting solid was collected by filtration and dried in vacuo to give 4-allyl-1-nicotinoylsemicarbazide as a colourless solid (37.1 g), m.p. 165–167° C.

1M Aqueous sodium hydroxide solution (175 ml) was added over 10 minutes to a stirred suspension of 4-allyl-1-nicotinoylsemicarbazide (17.2 g) in water (100 ml), then the stirred mixture was heated at 90–95° C. for 17 hours, cooled to ambient temperature, and acidified to pH 5 by the addition of 5M hydrochloric acid. The mixture was concentrated in vacuo, and the resulting solid was collected by filtration and dried in vacuo at ambient temperature to give 4-allyl-5-(3-pyridyl)-1,2,4-triazol-3(2H,4H)-one as an off-white solid (14 g), m.p. 120–125° C.

A solution of 4-allyl-5-(3-pyridyl)-1,2,4-triazol-3(2H,4H)-one (5 g) in dimethylformamide (50 ml) was added dropwise at ambient temperature under nitrogen to a stirred mixture of sodium hydride [0.92 g; 60% dispersion in mineral oil—pre-washed with petroleum ether (b.p. 40–60° C.)] and dimethylformamide (50 ml). The mixture was then stirred at ambient temperature for 1 hour, 1-bromo-4-chlorobutane (2.65 ml) was added, and stirring at ambient temperature was continued for 16 hours. The solvent was removed in vacuo, the residue was diluted with water (60 ml), and the product was extracted into ethyl acetate (2×200 ml). The extracts were dried (MgSO₄), and the solvent was removed in vacuo to leave 4-allyl-2-(4-chlorobutyl)-5-(3-pyridyl)-1,2,4-triazol-3(2H,4H)-one as a yellow oil (6.93 g).

A mixture of 4-allyl-2-(4-chlorobutyl)-5-(3-pyridyl)-1,2,4-triazol-3(2H,4H)-one (3 g), 1-(2-methoxyphenyl)piperazine monohydrochloride (2.3 g), potassium carbonate (2.76 g), potassium iodide (10 mg) and toluene (100 ml) was stirred at 90–95° C. under nitrogen for 85 hours. During this time, three further portions of 1-(2-methoxyphenyl)piperazine monohydrochloride (3×1.92 g) were added at 17 hourly intervals. The solvent was removed in vacuo, the residue was diluted with water (100 ml), and the product was extracted into ethyl acetate (3×50 ml). The extracts were dried (MgSO₄) and the solvent removed in vacuo to leave an oil which was purified by flash chromatography over silica using a 1:1 mixture of ether and methanol as eluant. Appropriate fractions were combined and the solvents removed in vacuo. The residue was triturated with ether, undissolved solid was removed by filtration, and the solvent was removed in vacuo. The residue was triturated with petroleum ether (b.p. 40–60° C.) and the resulting solid was collected by filtration and dried in vacuo at ambient temperature to give 4-allyl-2-{4-[4-(2-methoxyphenyl)piperazin-1-yl]butyl}-5-(3-pyridyl)-1,2,4-triazol-3(2H,4H)-one as an off-white solid (1 g), m.p. 71–75° C.

EXAMPLES 47–63

The following compounds of formula I, in which A is methylene and HET is a group of formula d), were prepared by method Da below:

| Example No | Name |
|---|---|
| 47 | 4-Allyl-2-[4-(2-methoxyphenyl)piperazin-1-ylmethyl]-5-(3-pyridyl)-1,2,4-triazole-3(2H,4H)-thione |
| 48 | 5-(4-Chlorophenyl)-2-[4-(2-methoxyphenyl)piperazin-1-ylmethyl]-4-(3-pyridyl)-1,2,4-triazole-3(2H,4H)-thione |
| 49 | 4-Allyl-2-[4-(2-methoxyphenyl)piperazin-1-ylmethyl]-5-(4-pyridyl)-1,2,4-triazole-3(2H,4H)-thione |
| 50 | 2-[4-(2-Methoxyphenyl)piperazin-1-ylmethyl]-4-(3-methoxypropyl)-5-(4-pyridyl)-1,2,4-triazole-3(2H,4H)-thione |
| 51 | 2-[4-(2-Methoxyphenyl)piperazin-1-ylmethyl]-4-methyl-5-(4-pyridyl)-1,2,4-triazole-3(2H,4H)-thione |
| 52 | 4-Allyl-2-[4-(2-methoxyphenyl)piperazin-1-ylmethyl]-5-phenyl-1,2,4-triazole-3(2H,4H)-thione |
| 53 | 2-[4-(2-Methoxyphenyl)piperazin-1-ylmethyl]-4-propyl-5-(4-pyridyl)-1,2,4-triazole-3(2H,4H)-thione |
| 54 | 2-[4-(2-Methoxyphenyl)piperazin-1-ylmethyl]-4-methyl-5-(trifluoromethyl)-1,2,4-triazole-3(2H,4H)-thione |
| 55 | 2-[4-(2-Methoxyphenyl)piperazin-1-ylmethyl]-4-methyl-1,2,4-triazole-3(2H,4H)-thione |
| 56 | 4-Allyl-5-(2-furyl)-2-[4-(2-methoxyphenyl)piperazin-1-ylmethyl]-1,2,4-triazole-3(2H,4H)-thione |
| 57 | 4-Allyl-5-(3-pyridyl)-2-[4-(pyrimidin-2-yl)piperazin-1-ylmethyl]-1,2,4-triazole-3(2H,4H)-thione |
| 58 | 4-Allyl-2-[4-(2-methoxyphenyl)piperazin-1-ylmethyl]-5-(2-pyridyl)-1,2,4-triazole-3(2H,4H)-thione |
| 59 | 4-Allyl-2-[4-(2-methoxyphenyl)piperazin-1-ylmethyl]-5-methyl-1,2,4-triazole-3(2H,4H)-thione |
| 60 | 4-Allyl-2-[4-(2-methoxyphenyl)piperazin-1-ylmethyl]-5-(2-thienyl)-1,2,4-triazole-3(2H,4H)-thione |
| 61 | 4-Allyl-2-[4-(2,3-dimethylphenyl)piperazin-1-ylmethyl]-5-(3-pyridyl)-1,2,4-triazole-3(2H,4H)-thione |
| 62 | 4-Allyl-5-(4-chlorophenyl)-2-[4-(2-methoxyphenyl)piperazin-1-ylmethyl]-1,2,4-triazole-3(2H,4H)-thione |
| 63 | 4-Allyl-2-[4-(2-methoxyphenyl)piperazin-1-ylmethyl]-5-(3-pyridyl)-1,2,4-triazol-3(2H,4H)-one |

Method Da

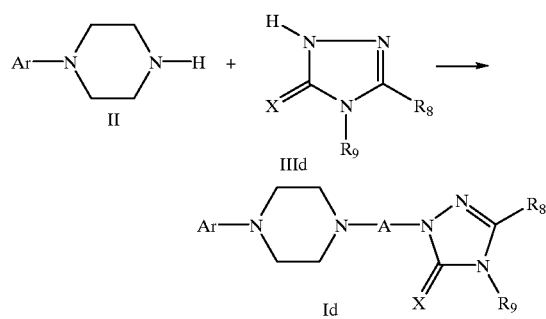

37% Aqueous formaldehyde solution (a ml) and a compound of formula II (b g) were added to a suspension of a compound of formula IIId (c g) in t-butanol (d ml) and the mixture was stirred at ambient temperature for e hours, then under reflux for f hours. The solvent was removed in vacuo to yield the crude product. In some cases the product was then purified by one or more of the following steps to give a compound of formula Id with a melting point as given in Table Da. Substituents and quantities are also given in Table Da.

Purification Steps i) The crude product was cooled and triturated with ether.

ii) Recrystallised first from a 1:1 mixture of propan-2-ol and ether, then from cyclohexane.

iii) The crude product was cooled and triturated with ethyl acetate.

iv) Recrystallised from propan-2-ol.

v) The crude product was cooled and triturated with a 1:1 mixture of water and propan-2-ol.

vi) Recrystallised from ethanol.

vii) Recrystallised from ethyl acetate.

viii) Flash column chromatography over silica using a 97:3 mixture of dichloromethane and methanol as eluant.

ix) Recrystallised from cyclohexane.

x) The ether filtrate from trituration was evaporated to leave a residue.

xi) The crude product was cooled and triturated with a 1:1 mixture of ether and petroleum ether (b.p. 40–60° C.).

xii) The crude product was cooled and triturated with a 2:1 mixture of ethanol and water.

xiii) The crude product was triturated with petroleum ether (b.p. 40–60° C.).

TABLE Da

| Ex No | Ar | X | R₈ | R₉ | a (ml) |
|---|---|---|---|---|---|
| 47 | 2-MeO-C₆H₄ | S | pyridin-3-yl | CH₂CH=CH₂ | 6.6 |
| 48 | 2-MeO-C₆H₄ | S | 4-Cl-C₆H₄ | pyridin-3-yl | 2.43 |
| 49 | 2-MeO-C₆H₄ | S | pyridin-4-yl | CH₂CH=CH₂ | 3.5 |
| 50 | 2-MeO-C₆H₄ | S | pyridin-4-yl | (CH₂)₃OMe | 2.7 |
| 51 | 2-MeO-C₆H₄ | S | pyridin-4-yl | Me | 3.8 |
| 52 | 2-MeO-C₆H₄ | S | Ph | CH₂CH=CH₂ | 0.9 |
| 53 | 2-MeO-C₆H₄ | S | pyridin-4-yl | Pr | 3.2 |
| 54 | 2-MeO-C₆H₄ | S | —CF₃ | Me | 1.9 |
| 55 | 2-MeO-C₆H₄ | S | H | Me | 1.9 |
| 56 | 2-MeO-C₆H₄ | S | furan-2-yl | CH₂CH=CH₂ | 3.7 |

TABLE Da-continued

| Ex No | Ar | X | HET-sub | alkenyl | result |
|---|---|---|---|---|---|
| 57 | pyrimidin-2-yl | S | pyridin-3-yl-CH2 | allyl | 25.4 |
| 58 | 2-MeO-phenyl | S | pyridin-2-yl-CH2 | allyl | 7.4 |
| 59 | 2-MeO-phenyl | S | Me | allyl | 6.0 |
| 60 | 2-MeO-phenyl | S | thien-2-yl-CH2 | allyl | 13.9 |
| 61 | 2,3-diMe-phenyl | S | pyridin-3-yl-CH2 | allyl | 3.65 |
| 62 | 2-MeO-phenyl | S | 4-Cl-phenyl-CH2 | allyl | 0.80 |
| 63 | 2-MeO-phenyl | O | pyridin-3-yl-CH2 | allyl | 3.40 |

| Ex No | b (g) | c (g) | d (ml) | e (hr) | f (hr) | purif step | m.p. (° C.) | yield (g) |
|---|---|---|---|---|---|---|---|---|
| 47 | 5.95 | 6.0 | 140 | 0.5 | 0.25 | i, ii | 97–99 | 2.49 |
| 48 | 1.82 | 2.5 | 60 | 0.5 | 0.33 | i | 170–178 | 3.88 |
| 49 | 2.21 | 2.5 | 60 | 0.75 | 0.33 | i | 143–145 | 4.55 |
| 50 | 1.92 | 2.5 | 60 | 0.5 | 0.33 | i | 100–104 | 3.51 |
| 51 | 2.50 | 2.5 | 60 | 0.5 | 0.33 | iii, iv | 137–139 | 2.63 |
| 52 | 2.10 | 2.16 | 45 | 1.5 | 16 | i | 98–100 | 2.44 |
| 53 | 2.19 | 2.5 | 60 | 0.5 | 0.25 | v | 97–100 | 3.10 |
| 54 | 3.5 | 3.0 | 80 | 0 | 2 | i | 100–103 | 2.40 |
| 55 | 3.5 | 1.9 | 80 | 0 | 0.66 | i | 114–117 | 3.96 |
| 56 | 0.76 | 0.82 | 25 | 0.5 | 0.33 | i, vi | 131–133 | 0.87 |
| 57 | 4.60 | 6.0 | 170 | 0.33 | 0.5 | vii, viii, | 137–139 | 9.88 |
| 58 | 1.51 | 1.71 | 50 | 0.5 | 0.33 | ix | 110–112 | 1.47 |
| 59 | 1.25 | 1.0 | 40 | 0.5 | 0.33 | i, x, i, iv | 128–129 | 0.71 |
| 60 | 2.88 | 3.34 | 90 | 0.5 | 0.33 | i, iv | 103.5–105.5 | 1.7 |
| 61 | 2.44 | 2.80 | 70 | 0.5 | 0.33 | xi, ix | 119–121 | 4.01 |
| 62 | 0.47 | 0.62 | 40 | 0.5 | 0.33 | xii | 80–83 | 0.22 |
| 63 | 2.30 | 2.5 | 60 | 0.33 | 0 | xiii | 92–96 | 2.7 |

EXAMPLES 64–72

The following compounds of Formula I, in which A is —(CH$_2$)$_n$— and HET is a group of formula d), were prepared by method Db below:

| Example No | Name |
|---|---|
| 64 | 4-Allyl-2-{4-[4-(2,3-dimethylphenyl)piperazin-1-yl]butyl}-5-(3-pyridyl)-1,2,4-triazol-3(2H,4H)-one 1.5 maleate |
| 65 | 4-Allyl-2-{2-[4-(2,3-dimethylphenyl)piperazin-1-yl]ethyl}-5-(3-pyridyl)-1,2,4-triazol-3(2H,4H)-one 2.8 hydrochloride |
| 66 | 4-Allyl-2-{4-[4-(2-methoxyphenyl)piperazin-1-yl]butyl}-5-phenyl-1,2,4-triazol-3(2H,4H)-one dihydrochloride |
| 67 | 4-Allyl-2-{2-[4-(2-methoxyphenyl)piperazin-1-yl]ethyl}-5-(3-pyridyl)-1,2,4-triazol-3(2H,4H)-one dihydrochloride |
| 68 | 4-Allyl-2-{2-[4-(2-methoxyphenyl)piperazin-1-yl]ethyl}-5-phenyl-1,2,4-triazol-3(2H,4H)-one monofumarate |
| 69 | 4-Allyl-2-{2-[4-(2-methoxyphenyl)piperazin-1-yl]ethyl}-5-(2-thienyl)-1,2,4-triazol-3(2H,4H)-one |
| 70 | 4-Allyl-2-{2-[4-(2-methoxyphenyl)piperazin-1-yl]ethyl}-5-methyl-1,2,4-triazol-3(2H,4H)-one |
| 71 | 4-Allyl-2-{2-[4-(2-methylphenyl)piperazin-1-yl]ethyl}-5-(3-pyridyl)-1,2,4-trizol-3(2H,4H)-one 1.5 fumarate |
| 72 | 4-Allyl-2-{3-[4-(2-methoxyphenyl)piperazin-1-yl]propyl}-5-(3-pyridyl)-1,2,4-triazol-3(2H,4H)-one trihydrochloride. |

Method Db

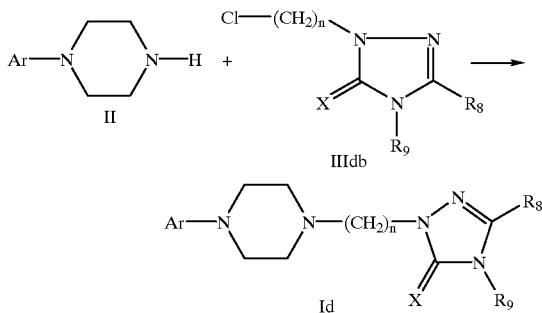

A compound of formula II (a g) was added to a mixture of a compound of formula IIId (b g), potassium carbonate (c g) and a catalytic amount of potassium iodide in dimethylformamide (d ml) under nitrogen. The mixture was stirred and heated at –95° C. for e hours. Water (100 ml) was added, and the product extracted into ethyl acetate (2×100 ml). The organic extracts were washed with water (2×100 ml), dried (MgSO$_4$) and concentrated in vacuo to yield an oil. The oil was purified by one or more of the following steps to yield a compound of formula Id with a melting point as given in Table Db. Substituents and quantities are also given in Table Db.

Purification Steps i) flash column chromatography over silica using a 1:1 mixture of methanol and ethyl acetate as eluant.

ii) the salt was recrystallised from a mixture of petroleum ether (b.p. 40–60° C.) and ethanol.

iii) flash column chromatography over silica using ethyl acetate as eluant to yield a solid.

iv) the solid was recrystallised from propan-2-ol.

v) column chromatography over silica using a 9:1 mixture of toluene and triethylamine as eluant.

vi) trituration with ether.

vii) the ether extract from the trituration had the solvent removed in vacuo.

viii) column chromatography over silica using a 9:1 mixture of dichloromethane and methanol as eluant.

ix) reduced pressure column chromatography over silica using a 2:1 mixture of ethyl acetate and methanol as eluant.

x) the salt was triturated with a 5:1 mixture of ethyl acetate and propan-2-ol.

TABLE Db

| Ex No | Ar | n | X | R$_8$ | R$_9$ | a (g) | b (g) | c (g) | d (ml) | e (hr) | purif. step | NB | m.p. (° C.) | yield (g) |
|---|---|---|---|---|---|---|---|---|---|---|---|---|---|---|
| 64 | 2,3-dimethylphenyl | 4 | O | 3-pyridyl | allyl | 2.28 | 3.54 | 3.32 | 100 | 72 | i | 1 | 97–99 | 2.01 |
| 65 | 2,3-dimethylphenyl | 2 | O | 3-pyridyl | allyl | 3.16 | 2.2 | 1.15 | 100 | 72 | i | 2 | 124–126 | 0.20 |

TABLE Db-continued

| Ex No | Ar | n | X | $R_8$ | $R_9$ | a (g) | b (g) | c (g) | d (ml) | e (hr) | purif. step | NB | m.p. (° C.) | yield (g) |
|---|---|---|---|---|---|---|---|---|---|---|---|---|---|---|
| 66 | 2-OMe-phenyl | 4 | O | Ph | allyl | 5.73 | 6.0 | 5.49 | 100 | 60 | i | 2 | 182–185 | 4.40 |
| 67 | 2-OMe-phenyl | 2 | O | Ph | allyl | 3.28 | 4.52 | 4.72 | 200 | 72 | i, ii | 2, 3 | 178–182 | 1.00 |
| 68 | 2-OMe-phenyl | 2 | O | pyridyl | allyl | 9.80 | 9.00 | 9.39 | 100 | 48 | i | 4, 3, 5 | 140–143 | 6.60 |
| 69 | 2-OMe-phenyl | 2 | O | thienyl | allyl | 3.23 | 4.54 | 4.64 | 50 | 70 | iii, iv, v, vi | 6, 7 | 92–94 | 1.04 |
| 70 | 2-OMe-phenyl | 2 | O | Me | allyl | 3.23 | 3.39 | 4.64 | 50 | 70 | vi, vii, vi, viii | 6, 7 | 87–89 | 1.36 |
| 71 | 2-Me-phenyl | 2 | O | pyridyl | allyl | 3.50 | 3.40 | 3.70 | 120 | 60 | ix | 8 | 140–142 | 2.51 |
| 72 | 2-OMe-phenyl | 3 | O | pyridyl | allyl | 2.30 | 3.40 | 3.30 | 100 | 48 | x, iv | 2 | 143–145 | 1.24 |

Notes to Table Db

1) The purified oil was dissolved in ether and an excess of ethereal maleic acid solution was added, resulting in the formation of the maleate salt.

2) The purified oil was taken up in ethanol (50 ml) and the solution was saturated with hydrogen chloride gas, resulting in the formation of the hydrochloride salt.

3) Water (200 ml) and ethyl acetate (3×100 ml) were used in the extraction.

4) The compound of formula II was in dimethylformamide (80 ml).

5) The purified oil was dissolved in propan-2-ol and added to a warm solution of fumaric acid (2.63 g) in propan-2-ol (100 ml), resulting in the formation of the fumarate salt.

6) Acetonitrile (120 ml) was included in the reaction mixture.

7) Instead of adding water and extracting the product, the mixture was filtered and the solvents were removed in vacuo to yield an oil.

8) The purified oil was dissolved in ethyl acetate and treated with fumaric acid (1.36 g) in industrial methylated spirit, resulting in formation of the fumarate salt.

Preparation of Starting Materials

Compounds of formula II

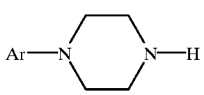

The compound of formula II in which Ar is 1,4-benzodioxan-5-yl was prepared in a similar manner to that described in Example 2.

The compound of formula II in which Ar is 7-benzo[b]furan-1-yl was prepared in the following manner:

A mixture of 2-bromophenol (34.8 ml), bromoacetaldehyde dimethyl acetal (35.5 ml), potassium carbonate (124.4 g) and dimethylformamide (500 ml) was stirred at 95° C. under nitrogen for 18 hours, then cooled and poured onto cold water (500 ml). The product was extracted into ether (2×300 ml) and the combined extracts were washed with saturated aqueous sodium bicarbonate solution (300 ml) and brine (300 ml) and dried (MgSO$_4$). The solvent was removed in vacuo to give 2-(2-bromophenoxy) acetaldehyde dimethyl acetal as an oil (69.6 g).

A mixture of phosphorus pentoxide (19.3 g) and phosphoric acid (64 ml, 85%) was added carefully to a stirred solution of 2-(2-bromophenoxy)acetaldehyde dimethyl acetal (69.6 g) in chlorobenzene (450 ml) at ambient temperature under nitrogen. The mixture was then heated under reflux for 20 hours, cooled and poured into ice/water (500 ml). The aqueous layer was separated and washed with dichloromethane (2×250 ml). The combined organic extracts were washed with brine (400 ml), dried (MgSO$_4$), and the solvent removed in vacuo. The residue was purified by flash column chromatography over silica using a 1:49 mixture of ether and petroleum ether (b.p. 60–80° C.) as the eluant, followed by distillation to give 7-bromobenzo[b]furan (30.3 g) as a clear oil, b.p. 66–68° C. at 0.93 mbar.

Tri-o-tolylphosphine (1.42 g) was added to a stirred suspension of bis (dibenzylideneacetone) palladium (O) (1.4 g) in toluene (480 ml) at ambient temperature under nitrogen. Sodium tert-butoxide (16.1 g) was added, followed by N-tert-butoxycarbonylpiperazine (26.6 g) and stirring was continued at ambient temperature for 5 minutes. 7-Bromobenzo[b]furan (23.3 g) was added and the stirred mixture was heated under reflux for 20 hours and then cooled to ambient temperature. The organic solution was decanted from the palladium residues, then washed with brine (500 ml) and dried (MgSO$_4$). The solvent was removed in vacuo and the residue was purified by flash column chromatography over silica using a 1:9 mixture of ether and petroleum ether (b.p. 60–80° C.) as eluant to give tert-butyl 4-(7-benzo[b]furanyl)piperazine-1-carboxylate (7.12 g) as a pale yellow solid, m.p. 98–100° C.

Trifluoroacetic acid (5 ml) was added dropwise at 20° C. under nitrogen to a cooled solution of tert-butyl 4-(7-benzo[b]furanyl)piperazine-1-carboxylate (1.66 g) in dichloromethane (5 ml). The solution was stirred at ambient temperature for 1 hour, then poured into cold water (50 ml). The mixture was basified by the addition of aqueous ammonia solution, then the product was extracted into dichloromethane (2×50 ml). The combined organic extracts were washed with brine (100 ml), dried (MgSO$_4$), and the solvent removed in vacuo to give 1-(7-benzo[b]furanyl)piperazine (1.02 g).

Other compounds of formula II are known and/or commercially available.

Compounds of formula IIIa

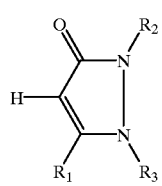

IIIa

| R$_1$ | R$_2$ | R$_3$ | Method |
|---|---|---|---|
| NH$_2$ | Ph | Me | IIIai |
| NH$_2$ | Ph | Pr | IIIaii |
| NH$_2$ | Ph | 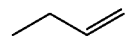 | IIIaiii |

Phenylhydrazine (75 g) was added dropwise at <20° C. to stirred acetic acid (198 ml). When the addition was complete, formamide (27.9 ml) was added in one portion, and the mixture was stirred at ambient temperature for 4 hours. Water (225 ml) was added, and the resulting solid was collected by filtration, washed well with water, and dried in vacuo to give N'-phenylformohydrazide (68.8 g) as a cream solid, m.p. 138–143° C.

A solution of N'-phenylformohydrazide (20.59 g) in dry tetrahydrofuran (750 ml) was added dropwise under nitrogen to a stirred suspension of lithium aluminium hydride (10 g) in dry tetrahydrofuran (200 ml), then the mixture was stirred and heated under reflux for 4 hours. The mixture was quenched by the slow dropwise addition of water (10 ml), followed by 5M aqueous sodium hydroxide solution (10 ml), then water (20 ml), then it was filtered, dried (MgSO$_4$) and the solvent removed in vacuo to yield an oil. The oil was dissolved in ether, redried (MgSO$_4$) and the solvent removed in vacuo to yield 1-methyl-2-phenylhydrazine (14.1 g) as a yellow oil.

A solution of sodium methoxide (6.88 g) in methanol (30 ml) was added dropwise at 0–5° C. under nitrogen to a stirred solution of ethyl 3-amino-3-ethoxyacrylate hydrochloride (21.8 g) in methanol (120 ml). A solution of 1-methyl-2-phenylhydrazine (13.63 g) in methanol (30 ml) was then added dropwise at 0–5° C. and the mixture was stirred at 0–5° C. for 2 hours, at ambient temperature for 20 hours, and at reflux temperature for 48 hours. The mixture was then poured into ice water (300 ml) and the product extracted into dichloromethane. The extracts were dried (MgSO$_4$) and the solvent removed in vacuo to give an oil which was triturated with a 5:1 mixture of ether and propan-2-ol to give 3-amino-2-methyl-1-phenyl-3-pyrazolin-5-one as a solid (4.5 g), m.p. 205–215° C.

IIIaii

Potassium carbonate (39.3 g) was added in one portion to a stirred, ice-cooled suspension of 5-amino-1-phenyl-3-pyrazolin-5-one (10 g) in dry acetonitrile (75 ml) and the mixture stirred for 30 minutes. Propyl iodide (6.6 ml) was added dropwise and the mixture was stirred at ambient temperature for 1 hour, then at reflux temperature for 1.5 hours. Further propyl iodide (3 ml) was added and the mixture was stirred and heated under reflux for 2 hours, then allowed to cool to ambient temperature. The resulting solid was collected by filtration, washed with acetonitrile (150 ml) and water (100 ml), then dried in vacuo at 65° C. to yield 3-amino-1-phenyl-2-propyl-3-pyrazolin-5-one as a white solid (3.25 g), m.p. 183–185° C.

IIIaiii

Sodium hydride (2.5 g) was added in portions over 10 minutes under nitrogen to a stirred, ice-cold suspension of 5-amino-1-phenyl-3-pyrazolin-5-one (10 g) in dry tetrahydrofuran (100 ml) and the mixture was stirred for 1 hour. Allyl bromide (6.4 ml) was added dropwise and the cooled mixture stirred for 1 hour. Further allyl bromide (2.66 g) was added and the mixture stirred at ambient temperature for 72 hours, then at reflux temperature for 1 hour. Allyl bromide (2.66 g) was added, and the mixture stirred for a further 1.5 hours at reflux temperature. Sodium hydride (1.2 g) was added and the mixture was stirred at ambient temperature overnight. Water (10 ml) was added, and the solution removed by decantation from the resulting solid. The solvents were removed in vacuo and the residue combined with the solid. The crude product was suspended in a mixture of dichloromethane (50 ml) and water (25 ml) and stirred for 1 hour. The resulting solid was collected by filtration and dried in vacuo at 65° C. to give 2-allyl-3-amino-1-phenyl-3-pyrazolin-5-one (1.9 g) as a cream solid m.p. 184–185° C.

Compounds of formula IIIb

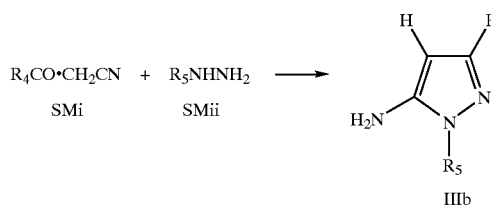

A mixture of a compound of formula SMi (a g) and a compound of formula SMii (b g) in ethanol (c ml) was heated under reflux for d hours, then cooled and concentrated in vacuo. The residue was purified by flash column chromatography over silica using a mixture of ethyl acetate and petroleum ether (b.p. 60–80° C.) as eluant to yield the compound of formula IIIb. The details are given in Table IIIb.

Notes to Table IIIb

1) The product was recrystallised from a mixture of ether and petroleum ether (b.p. 40–60° C.).

2) The residue was triturated with cold ether.

3) The solid was recrystallised from ethyl acetate.

4) Eluant was a mixture of dichloromethane and methanol.

5) Triethylamine (1 equivalent) was included in the reaction mixture.

6) Eluant was a mixture of ethyl acetate and methanol.

7) The residue was used without purification.

8) A solid precipitated from the cooled reaction mixture. This was collected by filtration and further purified by chromatography.

9) The hydrazine hydrochloride salt was used in the reaction.

TABLE IIIb

| $R_1$ | $R_4$ | $R_5$ | a (g) | b (g) | c (ml) | d (hr) | eluant mixture | Yield (g) | notes |
|---|---|---|---|---|---|---|---|---|---|
| $NH_2$ | cyclopropyl | Ph | | | Commercially Available | | | | |
| $NH_2$ | cyclopropyl | 4-Cl-phenyl | 2.14 | 2.8 | 25 | 5 | — | 2.8 | 1 |
| $NH_2$ | cyclopropyl | 2-Cl-phenyl | 5.05 | 6.6 | 72 | 16 | 1:2 | 3.83 | 3 |
| $NH_2$ | cyclopropyl | 4-OMe-phenyl | 2.4 | 3.05 | 35 | 6 | 3:7 | 1.85 | |
| $NH_2$ | cyclopropyl | 4-CN-phenyl | 2 | 2.44 | 25 | 12 | 100:1 | 1.71 | 8, 4 |
| $NH_2$ | cyclopropyl | 2-pyridyl | 1.2 | 1.2 | 15 | 6 | 1:4 | 1.79 | |
| $NH_2$ | cyclopropyl | 4-pyridyl | 6.95 | 9.28 | 100 | 16 | 97:3 | 1.57 | 9, 5, 6 |

TABLE IIIb-continued

| $R_1$ | $R_4$ | $R_5$ | a (g) | b (g) | c (ml) | d (hr) | eluant mixture | Yield (g) | notes |
|---|---|---|---|---|---|---|---|---|---|
| $NH_2$ | cyclopropyl | 2-pyrimidinyl | 1.88 | 2.54 | 30 | 16 | 95:5 | 1.45 | 9, 5, 6 |
| $NH_2$ | cyclopropyl | —$CH_2Ph$ | 1.96 | 2.20 | 30 | 4 | — | 3.66 | 7 |
| $NH_2$ | cyclopropyl | Me | | | Commercially Available | | | | |
| $NH_2$ | cyclopropyl | $Bu^t$ | 1.09 | 0.88 | 15 | 6 | 1:4 | 0.9 | — |
| $NH_2$ | cyclobutyl | Ph | 2.0 | 1.76 | 20 | 16 | 1:4 | 2.45 | — |
| $NH_2$ | cyclobutyl | Me | 2.0 | 0.75 | 20 | 16 | — | 2.1 | 2 |
| $NH_2$ | cyclopentyl | Ph | 3.0 | 1.96 | 50 | 5 | 3:7 | 1.79 | — |
| $NH_2$ | cyclopentyl | Me | 8.05 | 2.70 | 150 | 5 | — | 5.65 | 2 |
| $NH_2$ | $Bu^t$ | Ph | 10 | 9.20 | 150 | 10 | 3.7 | 5.3 | — |
| $NH_2$ | Ph | Ph | | | Commercially Available | | | | |
| $NH_2$ | Ph | Me | | | Commercially Available | | | | |

SMi

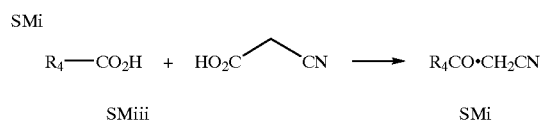

$R_4$—$CO_2H$ + $HO_2C$\~$CN$ → $R_4CO·CH_2CN$

SMiii                      SMi

Some compounds of formula SMi are commercially available. Others were prepared by the following method:

1,1-Carbonyldiimidazole (a g) was added to a compound of formula SMiii (b ml) in tetrahydrofuran (c ml) which was ice-cooled, and the mixture stirred for d hours at ambient temperature (mixture 1). Isopropylmagnesium chloride (e ml; 2M in tetrahydrofuran) was added to a solution of cyanoacetic acid (f g) in a mixture of dichloromethane (g ml) and tetrahydrofuran (h ml) over 1 hour under nitrogen at <15° C. The mixture was stirred for 2.5 hours, then mixture 1 was added dropwise and the mixture stirred at ambient temperature for 16 hours. The reaction was quenched by the addition of 3M hydrochloric acid (i ml) at <15° C. The mixture was stirred for 4 hours at ambient temperature then it was concentrated in vacuo to remove the organic solvents, and the product extracted into ether. The extracts were washed with aqueous sodium bicarbonate solution, then water, then dried ($MgSO_4$). The organic layer was filtered and the solvent removed in vacuo to yield the compound of formula Smi. The details are given in table SMi.

TABLE SMi

| $R_4$ | a (g) | b (ml) | c (ml) | d (hr) | e (ml) | f (g) | g (ml) | h (ml) | i (ml) | Yield (g) |
|---|---|---|---|---|---|---|---|---|---|---|
| cyclopropyl | 24.36 | 13.63 | 300 | 2.5 | 315 | 26.79 | 240 | 500 | 500 | 9.37 |
| cyclobutyl | 24.4 | 15 | 300 | 2 | 315 | 26.8 | 240 | 500 | 500 | 11.74 |

TABLE SMi-continued

| R4 | a (g) | b (ml) | c (ml) | d (hr) | e (ml) | f (g) | g (ml) | h (ml) | i (ml) | Yield (g) |
|---|---|---|---|---|---|---|---|---|---|---|
| 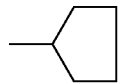 | 15 | 10 | 200 | 4 | 194 | 16.5 | 150 | 300 | 335 | 11.43 |

SMii

    SMii

Some compounds of formula SMii are commercially available. Others were prepared by the following method:

A compound of formula $R_5$—Cl (a g) was suspended in ethanol (b ml) and hydrazine hydrate (c ml) was added. The mixture was heated under reflux for d hours, allowed to cool to ambient temperature, then diluted with ether. The resulting solid was collected by filtration, washed with ether and dried in vacuo to yield a compound of formula Smii as the hydrochloride salt. The details are given in Table SMii.

TABLE SMii

| $R_5$ | a (g) | b (ml) | c (ml) | d (hr) | Yield (g) |
|---|---|---|---|---|---|
| 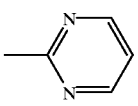 | 6.71 | 130 | 5.6 | 2 | 3.58 |
| 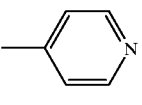 | 7.6 | 20 | 9 | 16 | 4.91 |

Compounds of formula IIIc

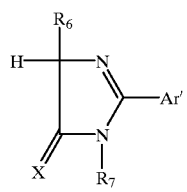    IIIc

The compound of formula IIIc in which X is O, $R_6$ is methyl, $R_7$ is H and Ar' is pyrid-3-yl was prepared in a similar manner to that described in Example 36.

The compound of formula IIIc in which X is O, $R_6$ is methyl, $R_7$ is H and Ar' is phenyl was prepared in a similar manner to that described in Example 37.

Compounds of formula IIId

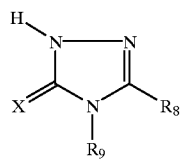    IIId

Compounds of formula IIId in which X is S, $R_8$ is pyrid-3-yl and $R_9$ is allyl, $R_8$ is pyrid-4-yl and $R_9$ is methyl, propyl, allyl or 3-methoxypropyl, $R_8$ is 4-chlorophenyl and $R_9$ is allyl or pyrid-3-yl, $R_8$ is trifluoromethyl and $R_9$ is methyl, and $R_8$ is H and $R_9$ is methyl are known and/or commercially available.

Compounds of formula IIId in which X is O were prepared in the following manner.

A semicarbazide of formula $R_9NHCONHNHCOR_8$ (a g) was suspended in water (b ml), 1M aqueous sodium hydroxide solution (c ml) was added, and the mixture was stirred at 95° C. for 17 hours then cooled. The mixture was acidified by the addition of 5M hydrochloric acid to pH 5, then concentrated in vacuo. The precipitate formed was the compound of formula IIId. The details are given in Table IIId TABLE IIId

| $R_8$ | $R_9$ | a (g) | b (ml) | c (ml) | Yield (g) |
|---|---|---|---|---|---|
|  |  | 17.2 | 100 | 175 | 14.0 |
| Ph |  | 30.0 | 60 | 300 | 21.7 |
|  |  | 10.0 | 57 | 100 | 7.6 |
| Me |  | 7.5 | 60 | 108 | 6.1 |

Other compounds of formula IIId in which X is S may be prepared by method IIIdi.

IIIdi

A mixture of 4-allyl-3-thiosemicarbazide (a g), a compound of formula $R_8CO_2Et$ (b g) and a solution of sodium methoxide (prepared from sodium (0.58 g) dissolved in methanol (50 ml)) was stirred and heated under reflux for 22 hours. The solvent was removed in vacuo to yield a gum. Water (70 ml) was added, and the resulting solid was collected by filtration, washed with water and dried in vacuo to yield a solid. Further solid was obtained by acidifying the filtrate and washings to pH 6 with glacial acetic acid (1.5 ml). The solid was the compound of formula IIId. The details are given in Table IIIdi.

Notes to Table IIIdi

1) Sodium (1.38 g), methanol (120 ml) and water (160 ml) were used.

2) The solid was recrystallised from industrial methylated spirit.

3) The mixture was heated under reflux for 39 hours.

4) The acidified filtrate and washings were concentrated to ⅓ volume and cooled to yield an oil. The oil was extracted into ethyl acetate (3×40 ml), the extracts dried (MgSO$_4$), and the solvent removed in vacuo to yield an oil. This was purified by flash column chromatography over silica using a 1:1 mixture of petroleum ether (b.p. 60–80° C.) and ethyl acetate to yield an oil which solidified on standing.

5) Sodium (0.87 g), methanol (75 ml) and water (200 ml) were used.

6) The crude product was suspended in a solution of sodium ethoxide prepared from sodium (0.6 g) in ethanol (50 ml) and the mixture was heated under reflux for 16 hours. Further sodium ethoxide prepared from sodium (0.6 g) in ethanol (50 ml) was added, and heating under reflux was continued for 72 hours. The solvent was removed in vacuo, the residue was diluted with ice-water (200 ml) and the mixture was acidified to pH 6 by the addition of acetic acid. The product was collected by filtration and dried in vacuo at 40° C. for 48 hours.

TABLE IIIdi

| $R_8$ | $R_9$ | X | a (g) | b (g) | notes | yield (g) |
|---|---|---|---|---|---|---|
| 2-pyridyl | allyl | S | 3.28 | 3.78 | — | 2.70 |
| 2-furyl | allyl | S | 3.28 | 3.18 | — | 0.82 |
| 2-thienyl | allyl | S | 7.86 | 9.36 | 1, 2 | 5.50 |
| Me | allyl | S | 3.28 | 4.40 | 3, 4 | 1.60 |
| Ph | allyl | S | 5.00 | 5.17 | 5, 6 | 2.20 |

Compounds of formula IIIdb

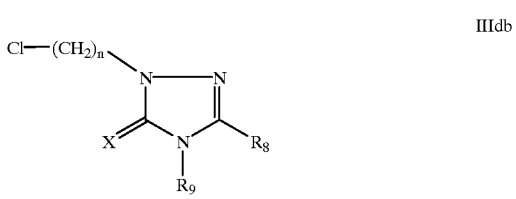

Compounds of formula IIIdb in which X is O were prepared from compounds of formula IIId in which X is O by the following method:

A solution of a compound of formula IIId (a g) in dimethylformamide (b ml) was added dropwise at ambient temperature under nitrogen to a stirred suspension of sodium hydride (c g; 60% oil dispersion) in dimethylformamide (d ml) then the mixture was stirred at ambient temperature for 1 hour. A compound of formula $Br(CH_2)_nCl$ (e ml) was added dropwise and the resulting mixture stirred at ambient temperature for 16 hours. Water (f ml) was added and the product extracted into ethyl acetate (3×100 ml). The extracts were washed with water (2×150 ml), dried ($MgSO_4$) and the solvent removed in vacuo to yield the compound of formula IIIdb. The details are given in Table IIIdb.

TABLE IIIdb

| $R_8$ | $R_9$ | n | a (g) | b (ml) | c (g) | d (ml) | e (ml) | f (ml) | Yield (g) |
|---|---|---|---|---|---|---|---|---|---|
| 4-pyridyl | allyl | 2 | 5.68 | 60 | 0.84 | 40 | 2.91 | 100 | 2.4 |
| 3-pyridyl | allyl | 3 | 3.00 | 50 | 0.64 | 30 | 1.48 | 60 | 3.4 |
| 4-pyridyl | allyl | 4 | 2.75 | 50 | 0.68 | 30 | 1.98 | 80 | 3.5 |
| 2-thienyl | allyl | 2 | 3.50 | 50 | 0.72 | 30 | 1.41 | 100 | 7.0 |
| Ph | allyl | 2 | 5.0 | 60 | 1.00 | 50 | 1.78 | 80 | 4.7 |
| Ph | allyl | 4 | 5.0 | 100 | 1.00 | 50 | 2.88 | 150 | 6.3 |
| Me | allyl | 2 | 3.5 | 50 | 1.08 | 30 | 2.10 | 100 | 6.5 |

EXAMPLE 79

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose are de-aggregated and blended. The mixture is filled into hard gelatin capsules, each capsule containing a unit dose of part of a unit dose of active compound.

b) Tablets

Tablets are prepared from the following ingredients.

|  | Parts by weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinyl-pyrrolidone in ethanol. The dry granulate is blended with the magnesium stearate and the rest of the starch. The mixture is then compressed in a tabletting machine to give tablets each containing a unit dose or a part of a unit dose of active compound.

Enteric coated tablets

Tablets are prepared by the method described in (b) above. The tablets are enteric coated in a conventional manner using a solution of 20% cellulose acetate phthalate and 3% diethyl phthalate in ethanol:dichloromethane (1:1).

d) Suppositories

In the preparation of suppositories, 100 parts by weight of active compound is incorporated in 1300 parts by weight of triglyceride suppository base and the mixture formed into suppositories each containing a therapeutically effective amount of active ingredient.

What is claimed is:

1. A compound of formula I

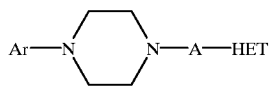

I or a pharmaceutically acceptable salt thereof in the form of an individual enantiomers, or racemates or other mixtures of enantiomers, in which HET represents a group of formula a)

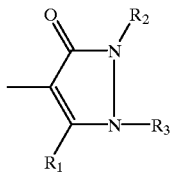

a)

in which $R_1$ represents hydroxy, an alkoxy group having 1 to 3 carbon atoms, or an amino group optionally substituted by one or two alkyl groups each having 1 to 3 carbon atoms; $R_2$ and $R_3$ independently represent an alkyl group having 1 to 6 carbon atoms optionally substituted by one or more halo, an alkenyl group having 2 to 6 carbon atoms optionally substituted by one or more halo, a cycloalkyl group having 3 to 6 carbon atoms, or phenyl, benzyl or a 5 or 6-membered heteroaryl group having 1 to 3 heteroatoms selected from O, N and S wherein the phenyl, benzyl or heteroaryl group may be optionally substituted by one or more substituents selected from a) halo, b) an alkyl group having 1 to 3 carbon atoms optionally substituted by one or more halo, c) an alkoxy group having 1 to 3 carbon atoms optionally substituted by one or more halo, d) an alkylthio group, an alkylsulphinyl group or an alkylsulphonyl group each having 1 to 3 carbon atoms optionally substituted by one or more halo, e) hydroxy, f) an acyloxy group having 1 to 3 carbon atoms, g) a hydroxyalkyl group having 1 to 3 carbon atoms, h) cyano, i) an alkanoyl group having 1 to 6 carbon atoms, j) an alkoxycarbonyl group having 2 to 6 carbon atoms, k) a carbamoyl group or a carbamoylmethyl group each optionally $\underline{N}$-substituted by one or two alkyl groups each having 1 to 3 carbon atoms, l) a sulphamoyl or sulphamoylmethyl group each optionally $\underline{N}$-substituted by one or two alkyl groups each having 1 to 3 carbon atoms, or m) an amino group optionally substituted by one or two alkyl groups each having 1 to 3 carbon atoms; and Ar represents phenyl, pyridyl, pyrimidinyl, naphthyl, 1,4-benzodioxin-5-yl, 1,4-benzodioxan-5-yl, benzo-[$\underline{b}$]furan-7-yl, 2,3-dihydrobenzo[$\underline{b}$]furan-7-yl, benzo-[$\underline{b}$]thiophen-7-yl, 2,3-dihydrobenzo[$\underline{b}$]thiophen-7-yl or chroman-8-yl each of which may be optionally substituted by one or more substituents selected from a) halo, b) an alkyl group having 1 to 3 carbon atoms optionally substituted by one or more halo, c) an alkoxy group having 1 to 3 carbon atoms optionally substituted by one or more halo, d) an alkylthio group, an alkylsulphinyl group or an alkylsulphonyl group each having 1 to 3 carbon atoms optionally substituted by one or more halo, e) hydroxy, f) an acyloxy group having 1 to 3 carbon atoms, g) a hydroxyalkyl group having 1 to 3 carbon atoms, h) cyano, i) an alkanoyl group having 1 to 6 carbon atoms, j) an alkoxycarbonyl group having 2 to 6 carbon atoms, k) a carbamoyl group or a carbamoylmethyl group each optionally $\underline{N}$-substituted by one or two alkyl groups each having 1 to 3 carbon atoms, l) a sulphamoyl or sulphamoylmethyl group each optionally $\underline{N}$-substituted by one or two alkyl groups each having 1 to 3 carbon atoms, or m) an amino group optionally substituted by one or two alkyl groups each having 1 to 3 carbon atoms; and A represents an alkylene chain having 1 to 6 carbon atoms each of which may be optionally substituted by one or two alkyl groups each having 1 to 3 carbon atoms.

2. A compound of formula I as claimed in claim 1 in which HET represents a group of formula a) in which $R_1$ represents an amino group; $R_2$ represents phenyl optionally substituted by a) halo, b) an alkyl group containing 1 to 3 carbon atoms optionally substituted by one or more halo, or c) an alkoxy group containing 1 to 3 carbon atoms optionally substituted by one or more halo; and R₃ represents an alkyl group having 1 to 4 carbon atoms or allyl; and Ar represents naphthyl, 1,4-benzodioxan-5-yl, benzo[b]furan-7-yl, or phenyl optionally substituted by an alkyl group having 1 to 3 carbon atoms or an alkoxy group having 1 to 3 carbon atoms; and A is methylene.

3. A compound selected from the group consisting of 3-Amino-4-(4-(2-methoxyphenyl)piperazin-1-ylmethyl)-2-methyl-1-phenyl-3-pyrazolin-5-one; 3-Amino-4-(4-(1,4-benzodioxan-5-yl)piperazin-1-ylmethyl)-2-methyl-1-phenyl-3-pyrazolin-5-one; 3-Amino-2-methyl-4-(4-(2-methylphenyl)piperazin-1-ylmethyl)-1-phenyl-3-pyrazolin-5-one; 3-Amino-2-methyl-4-(4-(1-naphthyl)piperazin-1-ylmethyl-1-phenyl-3-pyrazolin-5-one; 3-Amino-4-(4-(1,4-benzodioxan-5-yl)piperazin-1-ylmethyl)-1-phenyl-2-propyl-3-pyrazolin-5-one; 2-Allyl-3-amino-4-(4-(1,4-benzodioxan-5-yl)piperazin-1-ylmethyl)-1-phenyl-3-pyrazolin-5-one; 3-Amino-4-(4-(7-benzo-(b)furanyl)piperazin-1-ylmethyl)-2-methyl-1-phenyl-3-pyrazolin-5-one; 3-Amino-4-(4-(2-isopropoxyphenyl)piperazin-1-ylmethyl)-2-methyl-1-phenyl-3-pyrazolin-5-one; or pharmaceutically acceptable salts thereof or in the form, where appropriate, of individual enantiomers, racemates, or other mixtures of enantiomers.

4. The compounds of formula I as defined in claim 3 which is

3-Amino-4-[4-(1,4-benzodioxan-5-yl)piperazin-1-ylmethyl]-2-methyl-1-phenyl-3-pyrazolin-5-one;

or pharmaceutically acceptable salts thereof in the form, where appropriate of individual enantiomers, racemates, or other mixtures of enantiomers.

5. A composition comprising a therapeutically effective amount of a compound of formula I as claimed in claim 1 or a salt thereof together with a pharmaceutically acceptable diluent or carrier.

6. A method of treating depression, anxiety, psychoses, tardive dyskinesia, Parkinson's disease, hypertension, Tourette's syndrome, obsessive-compulsive behaviour, panic attacks, social phobias, cardiovascular and cerebrovascular disorders, stress, or prostatic hypertrophy which comprises the administration of a therapeutically effective amount of a compound of formula I as claimed in claim 1 to a mammal, in need thereof.

7. A method, as defined in claim 6, for the treatment of schizophrenia.

8. A process for the preparation of compounds of formula I as defined in claim 1, comprising the reaction of a compound of formula II

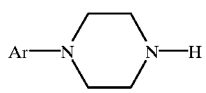

II with a compound of formula III

H—HET     III in the presence of formaldehyde in a suitable solvent, at a temperature in the range of from 0°–200° C.

* * * * *

UNITED STATES PATENT AND TRADEMARK OFFICE
CERTIFICATE OF CORRECTION

PATENT NO.    : 6,114,334
DATED         : September 5, 2000
INVENTOR(S)   : Kerrigan et al.

It is certified that error appears in the above-identified patent and that said Letters Patent is hereby corrected as shown below:

Column 75, claim 4,
Lines 27-28, delete "of formula I as defined in claim 3 which is".

Column 76, claim 6,
Line 11, delete "claimed" and substitute -- defined --.

Signed and Sealed this

Twenty-fifth Day of September, 2001

Attest:

NICHOLAS P. GODICI
Acting Director of the United States Patent and Trademark Office Attesting Officer